United States Patent [19]

Yamamoto

[11] Patent Number: 4,618,617

[45] Date of Patent: Oct. 21, 1986

[54] NOVEL 5-SUBSTITUTED 1,2,4,-OXADIAZOLE DERIVATIVES AND PREPARATION THEREOF

[75] Inventor: Michihiro Yamamoto, Nishinomiya, Japan

[73] Assignee: Sumitomo Chemical Company, Limited, Osaka, Japan

[21] Appl. No.: 469,511

[22] Filed: Feb. 24, 1983

[30] Foreign Application Priority Data

Mar. 3, 1982 [JP] Japan ................... 57-34168

[51] Int. Cl.$^4$ .................... C07D 271/06; A01K 31/41
[52] U.S. Cl. .................... 514/364; 544/138; 544/238; 544/333; 544/367; 546/277; 548/131; 548/132; 548/133
[58] Field of Search ............ 548/131, 132, 133; 514/364; 546/277; 544/138, 238, 333, 367

[56] References Cited

U.S. PATENT DOCUMENTS

| | | | |
|---|---|---|---|
| 3,697,530 | 10/1972 | Imai et al. | 260/295 R |
| 3,887,573 | 6/1975 | Breuer et al. | |
| 3,910,942 | 10/1975 | Narayanan | 548/131 |
| 4,069,332 | 1/1978 | Wright | 548/131 |

FOREIGN PATENT DOCUMENTS

| | | |
|---|---|---|
| 0054812 | 5/1981 | European Pat. Off. . |
| A0061882 | 10/1982 | European Pat. Off. . |
| 2343548 | 3/1974 | Fed. Rep. of Germany ...... 548/131 |
| 2457687 | 6/1976 | Fed. Rep. of Germany ...... 548/131 |
| 2748660 | 5/1978 | Fed. Rep. of Germany ...... 548/131 |
| 2801509 | 7/1979 | Fed. Rep. of Germany ...... 548/131 |
| 1559629 | 9/1967 | France . |
| 2018424 | 5/1970 | France . |
| 2451932 | 10/1980 | France .......................... 548/131 |
| 65881 | 3/1981 | Japan . |
| 1227978 | 4/1971 | United Kingdom . |
| 1271302 | 4/1972 | United Kingdom . |
| 615070 | 7/1978 | U.S.S.R. ....................... 548/131 |

OTHER PUBLICATIONS

Korbonits, J. Chem. Res. Synop. (2), 64 (1979), Abstract.
Chem. Abstracts, vol. 95, 1981, p. 673, 95:150674y.
Hynes, J. Med. Chem., 15, 1198 (1972).
Rieber, J. Heterocyclic Chem., 18, 1 (1981).

*Primary Examiner*—Robert Gerstl
*Attorney, Agent, or Firm*—Stevens, Davis, Miller & Mosher

[57] ABSTRACT

This disclosure describes novel 5-substituted 1,2,4-oxadiazoles useful as pharmaceuticals such as anti-inflammatory and analgesic agents.

18 Claims, No Drawings

NOVEL 5-SUBSTITUTED 1,2,4,-OXADIAZOLE DERIVATIVES AND PREPARATION THEREOF

This invention relates to novel 5-substituted 1,2,4-oxadiazole derivatives and processes for preparation thereof.

More particularly, the present invention pertains to 1,2,4-oxadiazole derivatives of the formula,

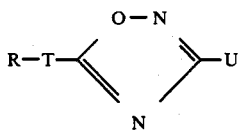

(I)

and a pharmaceutically acceptable salt thereof wherein R is a group selected from the group consisting of the following formulae (A), (B), (C), (D) and (E):

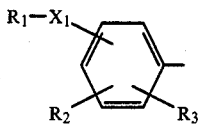

(A)

wherein $R_1$ is lower alkyl, lower alkenyl, lower cycloalkyl lower cycloalkenyl, phenyl, substituted phenyl or heterocyclic group; $R_2$ and $R_3$ are independently hydrogen, halogen, amino, hydroxy, lower alkoxy or lower alkyl; and $X_1$ is the radical $-CH_2-$, $-CH_2O-$, $>C=O$, $-O-$, $-S-$ or $-NH-$, or a single bond,

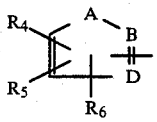

(B)

wherein $R_4$ and $R_5$ are independently hydrogen, lower alkyl, phenyl or substituted phenyl; $R_6$ is phenyl, substituted phenyl, benzoyl or substituted benzoyl; A is nitrogen, oxygen or sulfur; and B and D may be the same or different and are carbon or nitrogen,

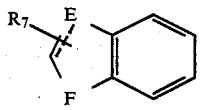

(C)

wherein $R_7$ is lower alkyl, lower alkoxy, phenyl or substituted phenyl; E is nitrogen or carbon; F is oxygen, sulfur or carbon, or a double bond of the formula $>C=C<$ or $>C=N-$; and the dotted line means a single bond or a double bond,

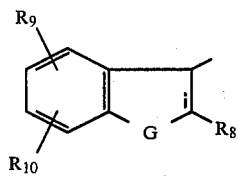

(D)

wherein $R_8$ is hydrogen or lower alkyl; $R_9$ is hydrogen, halogen or lower alkoxy; $R_{10}$ is hydrogen, cyclohexyl or substituted benzoyl; G is methylene, substituted benzoylimino, cinnamoylimino or substituted styrylidene, provided that when $R_{10}$ is cyclohexyl or substituted benzoyl G is methylene; and the dotted line means a single bond or a double bond, and

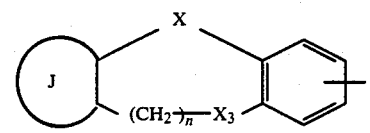

(E)

wherein $R_{11}$ is hydrogen, halogen, lower alkyl or lower alkoxy; $X_2$ and $X_3$ are different and selected from $-CH_2-$, $>C=O$, $-O-$, $-S-$, $-NH-$, $>N-CH_3$ and a single bond; J is an aromatic ring which is selected from the group consisting of benzene, pyridine, thiophene, furan and pyrrole; and n is 0 or 1; T is lower alkylene or lower alkenylene, both of which may bear an oxo, a hydroxy or a lower alkoxy radical on their carbon chains, or is a single bond; U is hydrogen, lower alkyl, lower alkenyl, polyhalo-lower alkyl, lower cycloalkyl, lower cycloalkenyl, phenyl, substituted phenyl, pyridyl, a group of the formula $R_{12}-T_1-$ [wherein $R_{12}$ is halogen, hydroxy, mercapto, lower alkylsulfinyl, di-lower alkoxymethyl, lower alkoxycarbonyl, carboxy, sulfo, cyano, the group

(wherein R' and R" are the same or different, and are hydrogen, lower alkyl, hydroxy-lower alkyl and when taken together with the adjacent nitrogen atom they may form a 5- or 6-membered saturated or unsaturated heterocyclic ring, which may contain another nitrogen or oxygen, or may form a quaternary ammonium salt or N-oxide), or the group

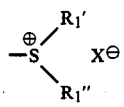

(wherein $R_1'$ and $R_1''$ are the same or different lower alkyl or lower alkenyl and X is a negative monovalent ion such as halide ion or sulfonate ion); and $T_1$ is lower alkylene or lower alkenylene, both of which may bear an oxo or a hydroxy group on their carbon chains], or a group of the formula $R_{13}-X_4-T_1-$ [wherein $R_{13}$ is lower alkyl, lower alkenyl, hydroxy-lower alkyl, acyloxy-lower alkyl, amino-lower alkyl, acylamino-lower alkyl, lower cycloalkyl, lower cycloalkenyl, phenyl, substituted phenyl, phenyl-lower alkyl, heterocyclic group, heterocyclic-lower alkyl, acyl, acylthio-lower alkanoyl, mercapto-lower alkanoyl, lower alkoxycarbonyl, lower alkylsulfonyl, the group

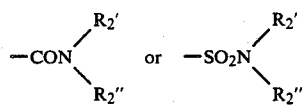

(wherein $R_2'$ and $R_2''$ are independently hydrogen, lower alkyl, or hydroxy-lower alkyl); $X_4$ is the radical $-O-$, $-S-$, $-NH-$,

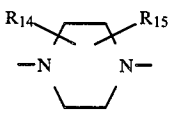

(wherein $R_{14}$ and $R_{15}$ are independently hydrogen or lower alkyl) or a single bond; and $T_1$ is as defined above].

In the compounds of the above formula (I) and elsewhere in the specification, the terms "alkyl", "alkenyl", "alkylene" and "alkenylene" mean both straight- and branched-$C_{1-6}$ hydrocarbon chains, and the lower alkyl may be $C_{1-6}$ alkyl such as methyl, ethyl, n-propyl, isopropyl, n-butyl, isobutyl, tert-butyl, n-pentyl, isopentyl, neopentyl, n-hexyl and the like. The lower alkenyl may be $C_{2-6}$ alkenyl such as vinyl, allyl, propenyl, isopropenyl, 2-methylpropenyl, 2-butenyl, prenyl and the like. The lower cycloalkyl may be an unsubstituted or oxo- or hydroxy-substituted $C_{3-6}$ alicyclic group such as cyclopropyl, cyclobutyl, cyclopentyl, 2-oxocyclopentyl, 2-hydroxycyclopentyl, cyclohexyl, 3-oxocyclohexyl and the like. The lower cycloalkenyl may be a $C_{5-6}$ unsaturated alicyclic group such as cyclopentenyl, cyclohexenyl or the like. The hydroxy-lower alkyl may, for example, be hydroxymethyl, 2-hydroxyethyl or 3-hydroxypropyl, and the lower alkoxy may, for example, be methoxy, ethoxy, n-propoxy, isopropoxy or n-butoxy. The term "halogen" includes all four halogens, i.e., fluorine, chlorine, bromine and iodine. The polyhalo-lower alkyl may, for example, be difluoromethyl, trichloromethyl, trifluoromethyl, chlorodifluoromethyl, 1,1,2,2-tetrafluoroethyl, 1,2,2,2-tetrafluoroethyl or pentafluoroethyl. The substituted phenyl means a phenyl group substituted by halogen, trifluoromethyl, hydroxy, $C_{1-6}$ alkyl, $C_{1-6}$ alkoxy and/or $C_{1-6}$ alkanoylamino, e.g., 2-chlorophenyl, 3-chlorophenyl, 4-chlorophenyl, 2-fluorophenyl, 4-fluorophenyl, 2,4-dichlorophenyl, 2,6-dichlorophenyl, 3-trifluoromethylphenyl, 2-methylphenyl, 4-methylphenyl, 2,3-dimethylphenyl, 4-hydroxyphenyl, 2-methoxyphenyl, 4-methoxyphenyl, and 4-acetylaminophenyl. The heterocyclic group may be pyridyl, thienyl, furyl, thiazolyl, imidazolyl, pyrazolyl, pyrrolyl, dihydropyrrolyl, pyrrolidinyl, oxazolyl, oxadiazolyl, benzothiazolyl, dihydrobenzothiazolyl, benzoxazolyl, isoindolinyl, imidazopyridyl, piperidyl, morpholinyl, pyrimidyl, pyridazinyl or the like, which may optionally be substituted by halogen, $C_{1-6}$ alkyl, amino, oxo, phenyl or the like, e.g., 2-pyridyl, 3-pyridyl, 4-pyridyl, 2-thienyl, 3-methyl-2-thienyl, 2-furyl, 2-thiazolyl, 2-amino-4-thiazolyl, 2-phenyl-4-thiazolyl, 1-imidazolyl, 4-methyl-5-imidazolyl, 2-oxazolyl, 1,2,4-oxadiazolyl, 1-pyrrolyl, 2,5-dihydro-1H-pyrrol-1-yl, benzothiazol-2-yl, 5-chloro-2,3-dihydro-2-oxobenzothiazol-3-yl, benzoxazol-2-yl, 1-oxo-2-isoindolinyl, or imidazo[1,2-a]pyridin-2-yl. The substituted benzoyl may be a benzoyl group substituted by halogen, $C_{1-6}$ alkyl, $C_{1-3}$ alkylenedioxy, $C_{1-6}$ alkylsulfinyl or the like, e.g., 4-chlorobenzoyl, 2-fluorobenzoyl, 4-fluorobenzoyl, 4-methylbenzoyl, 3,4-methylenedioxybenzoyl or 4-methylsulfinylbenzoyl. The acyl may be a substituted or unsubstituted $C_{2-4}$ alkanoyl group such as formyl, acetyl, propionyl, pivaloyl, hydroxyacetyl or 3-carboxypropionyl, and may also be an aroyl group such as benzoyl, substituted benzoyl or nicotinoyl. The substituted styrylidene may be a styrylidene group substituted by halogen, $C_{1-6}$ alkylsulfinyl or the like, e.g., 4-chlorostyrylidene or 4-methylsulfinylstyrylidene. In the present specification, the terms "lower alkylene" and "lower alkenylene" mean $C_{1-6}$ hydrocarbon chains which include an optical or a geometrical isomerism. The examples of the lower alkylene and alkenylene are illustrated as follows:

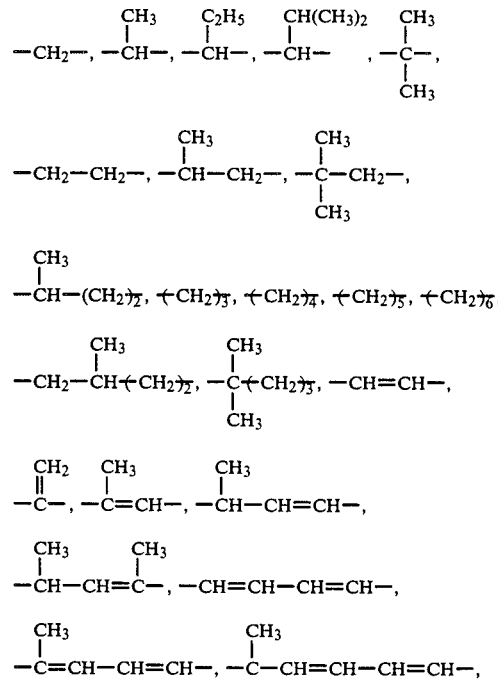

The quaternary ammonium salt of the group

is represented by the formula,

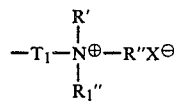

wherein $T_1$, $R'$ and $R''$ are as defined above, $R_1''$ is lower alkyl or lower alkenyl, and X is a negative monovalent ion such as halide ion or sulfonate ion. The term "sulfonate" as used herein means the negative radicals of organic sulfonic acids such as p-toluenesulfonic acid, methanesulfonic acid and the like.

This invention also includes acid addition salts of the compounds of the formula (I) formed with pharmaceutically acceptable acids. Such acids include both organic and inorganic acids, e.g., hydrochloric, hydrobromic, hydroiodic, sulfuric, phosphoric, methanesulfonic, acetic, pivalic, oxalic, maleic, fumaric, malic, succinic, tartaric, citric, ascorbic, glutamic, aspartic, stearic and palmitic acids and the like.

The oxadiazole derivatives of the formula (I) have not been reported in any literature, and they have been found to possess prominent pharmacological properties. In particular, they exhibit potent anti-inflammatory, analgesic, and antipyretic activities with significantly less side effects such as gastro-intestinal ulcerogenic activities. Therefore, the compounds of this invention are useful as anti-inflammatory and analgesic agents and are effective in the treatment of the inflammatory conditions in mammals.

The several 1,2,4-oxadiazole derivatives as illustrated below are heretofore disclosed to have anti-inflammatory activity. The compounds of this invention are, however, clearly different from those known compounds in chemical structure, especially in the substituents at 5-position of the oxadiazole ring.

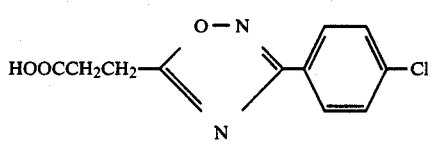

Belgian Patent 738,831

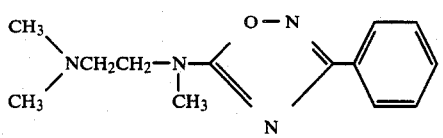

French Patent 1,559,629

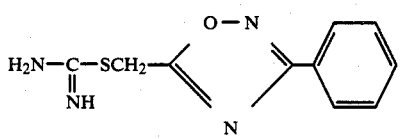

U.S. Pat. No. 3,887,573

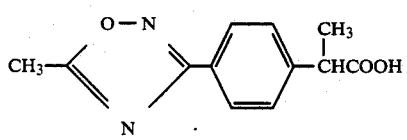

Japanese Patent Application
Kokai (Laid-Open) No. 65,881/81

Examples illustrating useful 5-substituents, which are represented by the group R-T- of the compounds of the formula (I), are:

(1) examples in which R is a group represented by the aforesaid formula (A),

| | |
|---|---|
| 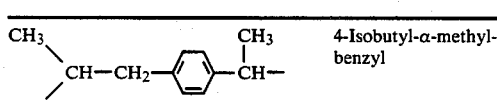 | 4-Isobutyl-α-methylbenzyl |
| 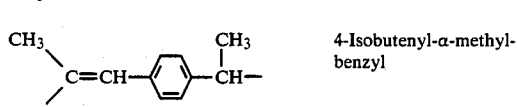 | 4-Isobutenyl-α-methylbenzyl |
| 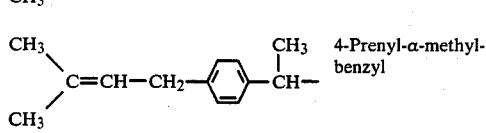 | 4-Prenyl-α-methylbenzyl |
|  | 4-Cyclohexyl-α-methylbenzyl |
|  | 3-Chloro-4-cyclohexyl-α-methylbenzyl |
| 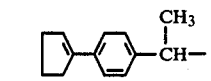 | 4-(1-Cyclopenten-1-yl)-α-methylbenzyl |
| 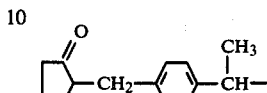 | 4-(2-Oxocyclopentan-1-ylmethyl)-α-methylbenzyl |
| 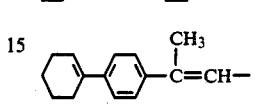 | 4-(1-Cyclohexen-1-yl)-β-methylstyryl |
| 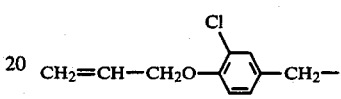 | 4-Allyloxy-3-chlorobenzyl |
| 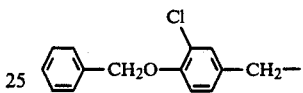 | 4-Benzyloxy-3-chlorobenzyl |
| 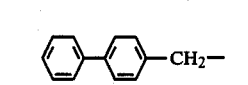 | 4-Biphenylylmethyl |
| 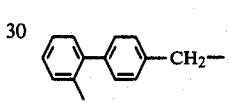 | 4-(2-Fluorophenyl)-benzyl |
| 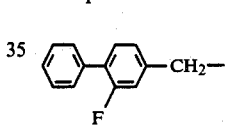 | 3-Fluoro-4-phenyl-benzyl |
| 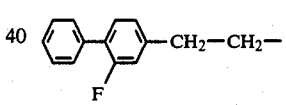 | 3-Fluoro-4-phenyl-phenethyl |
| 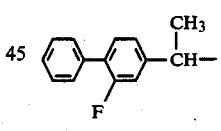 | 3-Fluoro-4-phenyl-α-methylbenzyl |
| 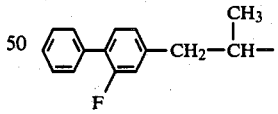 | 3-Fluoro-4-phenyl-α-methylphenethyl |
| 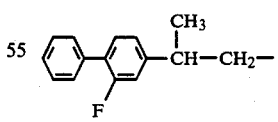 | 3-Fluoro-4-phenyl-β-methylphenethyl |
| 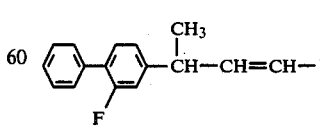 | 3-(2-Fluoro-4-biphenylyl)-1-butenyl |
| 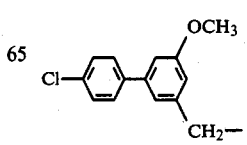 | 3-(4-Chlorophenyl)-5-methoxybenzyl |

| | |
|---|---|
| 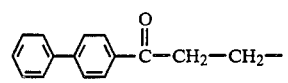 | 3-(4-Biphenylyl)-3-oxopropyl |
| 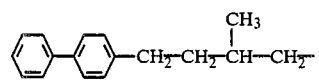 | 4-(4-Biphenylyl)-2-methylbutyl |
| 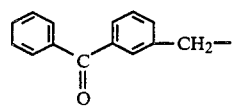 | 3-Benzoylbenzyl |
| 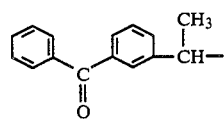 | 3-Benzoyl-α-methylbenzyl |
| 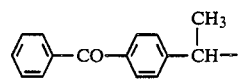 | 4-Benzoyl-α-methylbenzyl |
| 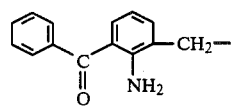 | 2-Amino-3-benzoylbenzyl |
| 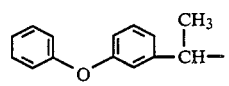 | 3-Phenoxy-α-methylbenzyl |
| 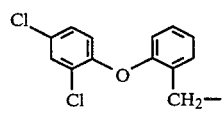 | 2-(2,4-Dichlorophenoxy)benzyl |
| 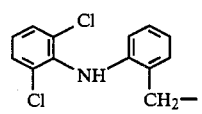 | 2-(2,6-Dichloroanilino)benzyl |
| 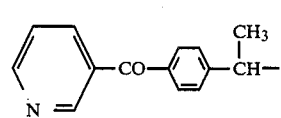 | 4-Nicotinoyl-α-methylbenzyl |
| 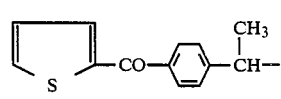 | 4-(2-Thenoyl)-α-methylbenzyl |
| 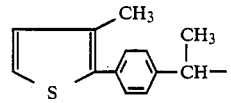 | 4-(3-Methyl-2-thienyl)-α-methylbenzyl |
| 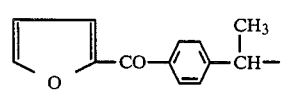 | 4-(2-Furoyl)-α-methylbenzyl |
| 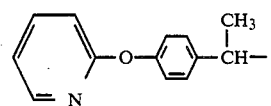 | 4-(2-Pyridyloxy)-α-methylbenzyl |
| 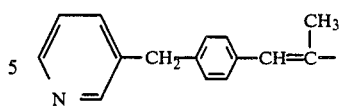 | 4-(3-Pyridylmethyl)-α-methylstyryl |
| 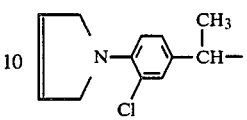 | 3-Chloro-4-(2,5-dihydro-1H—pyrrol-1-yl)-α-methylbenzyl |
| 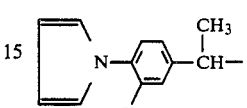 | 3-Chloro-4-(pyrrol-1-yl)-α-methylbenzyl |
| 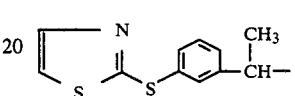 | 3-(2-Thiazolylthio)-α-methylbenzyl |
| 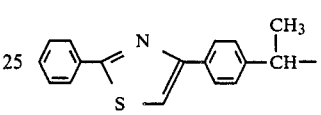 | 4-(2-Phenyl-4-thiazolyl)-α-methylbenzyl |
| 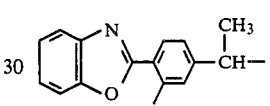 | 4-(Benzoxazol-2-yl)-3-fluoro-α-methylbenzyl |
| 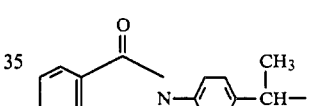 | 4-(1-Oxo-2-isoindolinyl)-α-methylbenzyl |
| 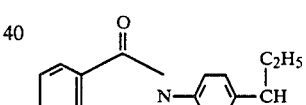 | 4-(1-Oxo-2-isoindolinyl)-α-ethylbenzyl |
| 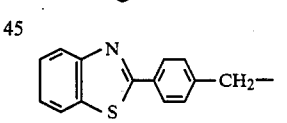 | 4-(Benzothiazol-2-yl)-benzyl |
| 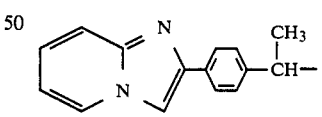 | 4-(Imidazo[1,2-a]-pyridin-2-yl)-α-methylbenzyl |
| 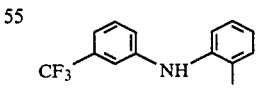 | 2-(3-Trifluoromethylanilino)phenyl |
| 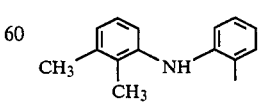 | 2-(2,3-Xylidino)phenyl |
| 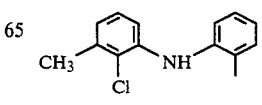 | 2-(2-Chloro-3-methylanilino)phenyl |

-continued

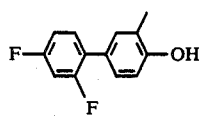 2',4'-Difluoro-4-hydroxy-3-biphenylyl (2) examples in which R is a group represented by the aforesaid formula (B),

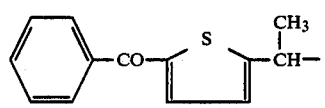 1-(5-Benzoyl-2-thienyl)ethyl

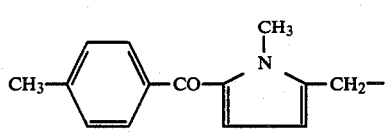 1-Methyl-5-toluoyl-2-pyrrolylmethyl

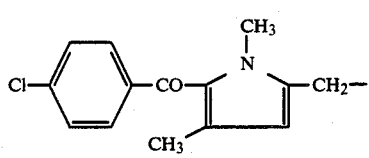 1,4-Dimethyl-5-(4-chlorobenzoyl)-2-pyrrolylmethyl

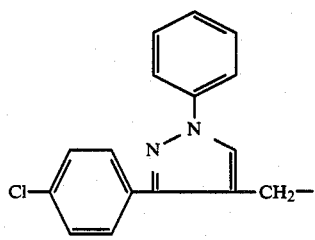 3-(4-Chlorophenyl)-1-phenyl-4-pyrazolylmethyl

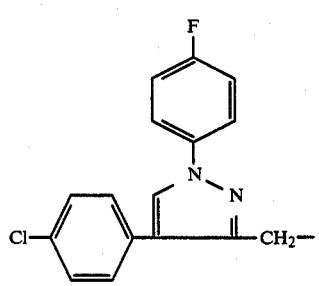 1-(4-Fluorophenyl)-4-(4-chlorophenyl)-3-pyrazolylmethyl

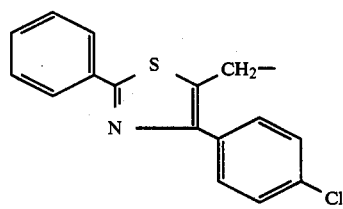 2-Phenyl-4-(4-chlorophenyl)-5-thiazolylmethyl

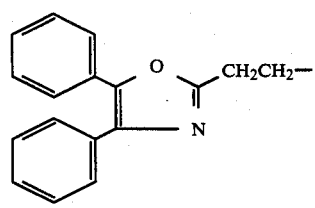 2-(4,5-Diphenyl-2-oxazolyl)ethyl (3) examples in which R is a group represented by the aforesaid formula (C),

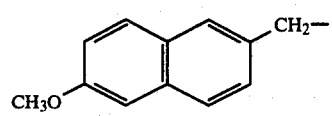 6-Methoxy-2-naphthylmethyl

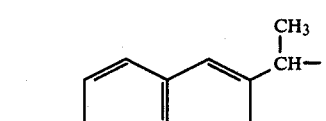 1-(6-Methoxy-2-naphthyl)ethyl

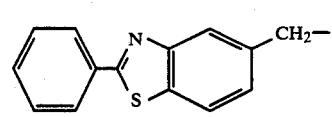 2-Phenylbenzothiazol-5-ylmethyl

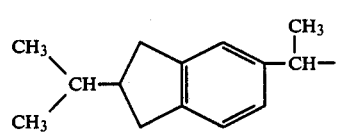 1-(2-Isopropylindan-5-yl)ethyl

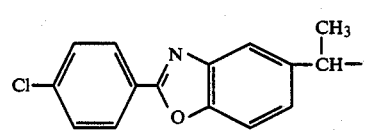 1-[2-(4-Chlorophenyl)benzoxazol-5-yl]ethyl

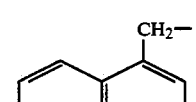 1-(4-Chlorophenyl)-5-isoquinolylmethyl

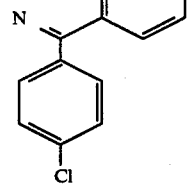

 1-(3-Phenylbenzofuran-7-yl)ethyl (4) examples in which R is a group represented by the aforesaid formula (D),

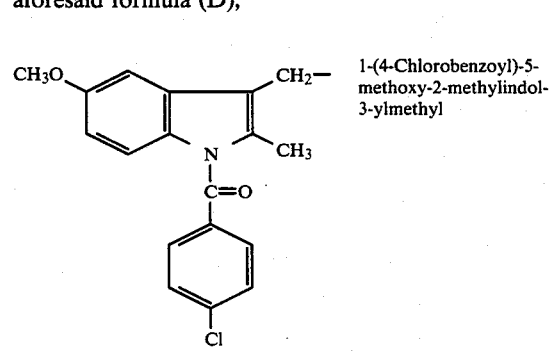 1-(4-Chlorobenzoyl)-5-methoxy-2-methylindol-3-ylmethyl

-continued
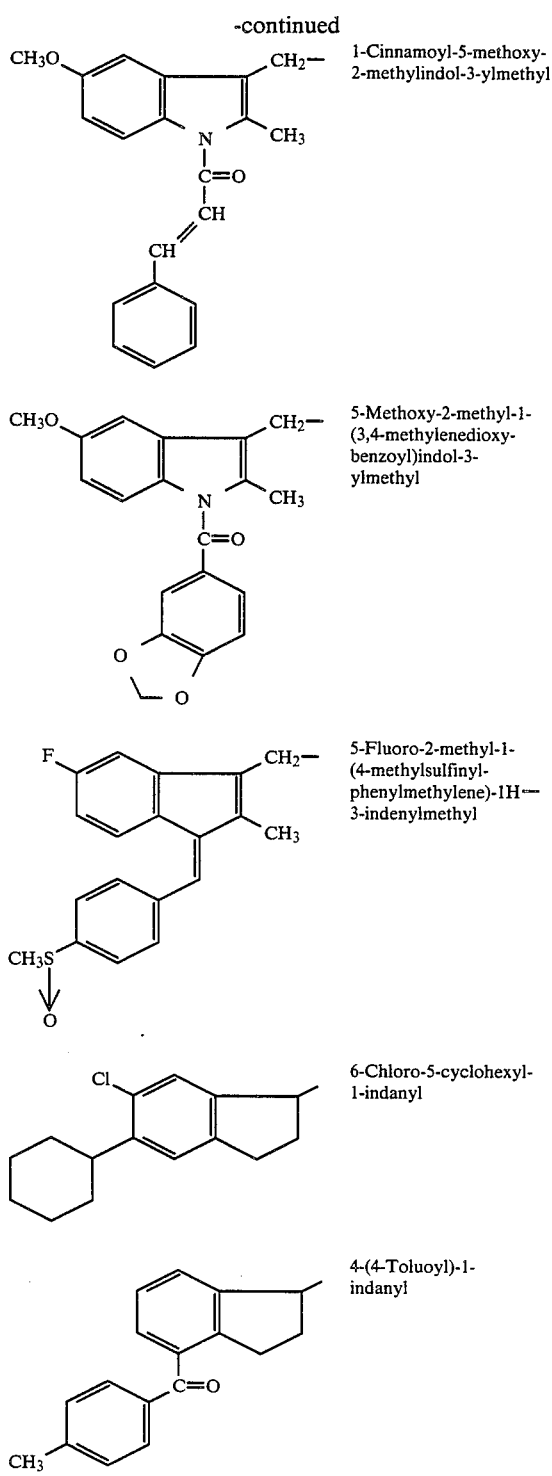
(5) examples to which R is a group represented by the aforesaid formula (E),
-continued
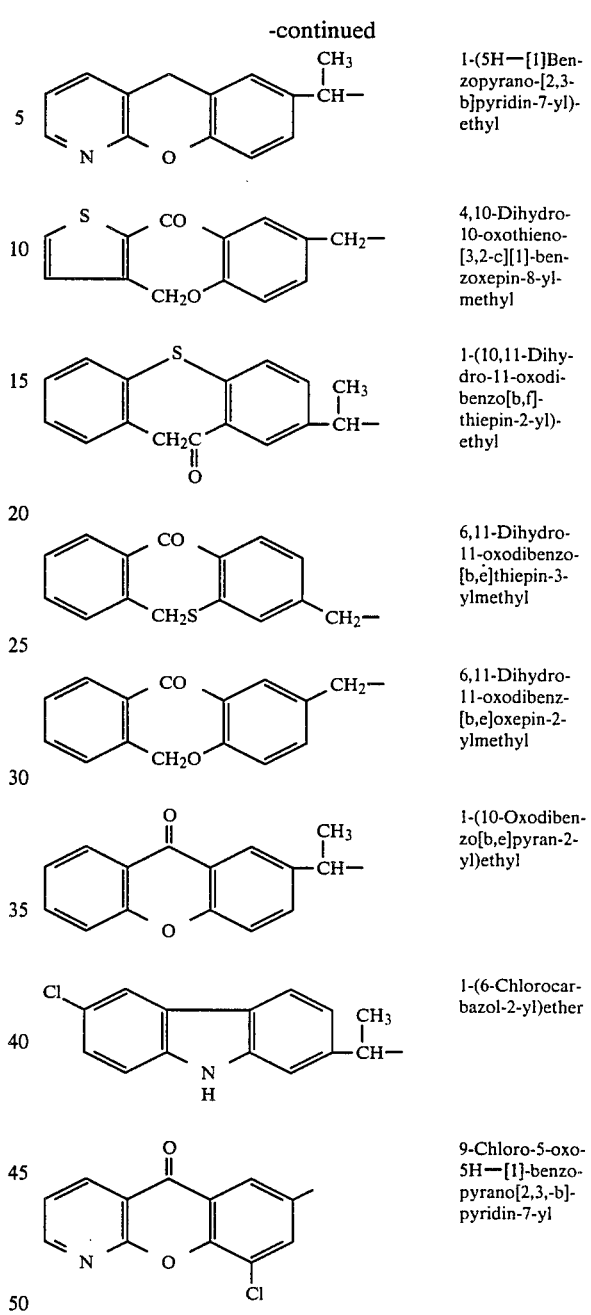
and the like.
Preferred compounds encompassed by the present invention include those of the formula (I) wherein R is
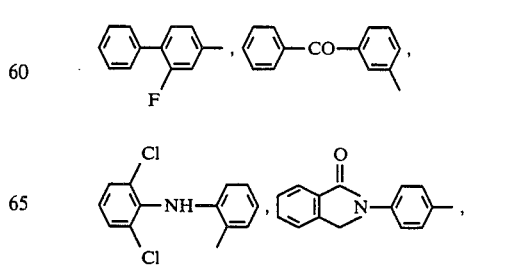

-continued

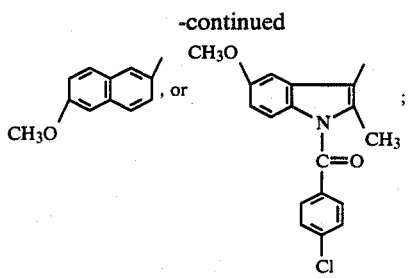, or 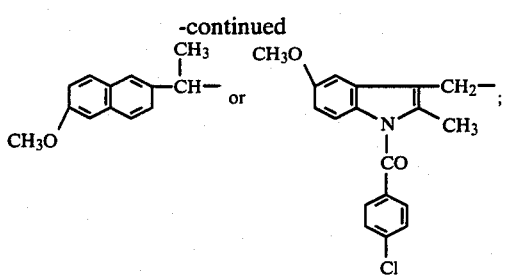

T is lower alkylene; and U is hydrogen, lower alkyl, lower alkenyl, lower cycloalkyl, polyhalo-lower alkyl, a group of the formula $R_{12}$-$T_1$-[wherein $R_{12}$ is halogen, hydroxy, mercapto, lower alkoxycarbonyl, carboxy, cyano, the group

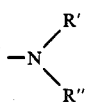

(wherein R' and R" are as defined above); and $T_1$ is lower alkylene] or a group of the formula $R_{13}$-$X_4$-$T_1$-[wherein $R_{13}$ is lower alkyl, lower alkenyl, hydroxy-lower alkyl, amino-lower alkyl, phenyl, phenyl-lower alkyl, heterocyclic-lower alkyl, acyl, mercapto-lower alkanoyl or

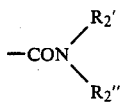

(wherein $R_2'$ and $R_2''$ are as defined above); $X_4$ is —O—, —S—, —NH— or

and $T_1$ is lower alkylene].

More preferred class of compounds falling within the scope of the formula (I) are those wherein the group R—T— is

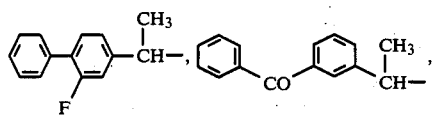

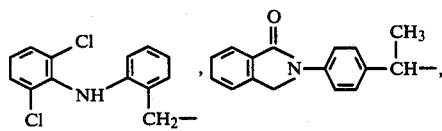

U is hydrogen, lower alkyl, hydroxy-lower alkyl, mercapto-lower alkyl,

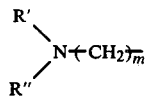

(wherein R' and R" are as defined above, and m is 1, 2 or 3) or $R_{13}$-$X_4$-$(CH_2)_{\overline{m}}$ (wherein $R_{13}$ is lower alkyl, hydroxy-lower alkyl, picolyl, acyl or mercaptolower alkanoyl; $X_4$ is —O—, —S—, —NH— or

and m is 1, 2 or 3).

Thus, it is apparent from the above description that most of the carboxylic acid derivatives of the formula,

R-T-COOH (II)

wherein R and T are as defined above, are known to possess anti-inflammatory and analgesic activities and many of them are now available for clinical uses. It is, however, well-known that said acidic nonsteroidal anti-inflammatory agents often cause gastrointestinal ulcer and other adverse effects. The oxadiazole derivatives of the formula (I) of this invention have surprisingly been found to show potent anti-inflammatory activity comparable to the known acidic anti-inflammatory drugs with remarkably less gastrointestinal adverse effects. The pharmacological test results of the following representative compounds are set forth in Table I.

Compound A: 5-(3-Fluoro-4-phenyl-α-methylbenzyl)-3-methyl-1,2,4-oxadiazole

Compound B: 5-(3-Fluoro-4-phenyl-α-methylbenzyl)-3-isobutyl-1,2,4-oxadiazole

Compound C: 3-Dimethylaminomethyl-5-(3-fluoro-4-phenyl-α-methylbenzyl)-1,2,4-oxadiazole Compound D: 5-(3-Fluoro-4-phenyl-α-methylbenzyl)-3-pyrrolidinomethyl-1,2,4-oxadiazole Compound E: 5-(3-Benzoyl-α-methylbenzyl)-3-methyl-1,2,4-oxadiazole Compound F: 5-(3-Benzoyl-α-methylbenzyl)-3-isobutyl-1,2,4-oxadiazole Compound G: 5-[1-(4-Chlorobenzoyl)-5-methoxy-2-methylindol-3-ylmethyl]-3-pyrrolidinomethyl-1,2,4-oxadiazole

TABLE I

| Compound | Carrageenin Paw Edema $ED_{30}$ (mg/kg) | Adjuvant Arthritis MED (mg/kg) | Ulceration of Small Intestine $UD_{50}$ (mg/kg) |
|---|---|---|---|
| A | 3.0 | 1.0 | 240 |

TABLE I-continued

| Compound | Carrageenin Paw Edema $ED_{30}$ (mg/kg) | Adjuvant Arthritis MED (mg/kg) | Ulceration of Small Intestine $UD_{50}$ (mg/kg) |
| --- | --- | --- | --- |
| B | 2.8 | 1.0 | >400 |
| C | 0.7 | 1.0 | 70 |
| D | 0.5 | 1.0 | 18 |
| E | 2.1 | 0.5 | 36 |
| F | 5.4 | 1.0 | 200 |
| G | 2.1 | 0.5 | 19 |
| Flurbiprofen | 0.8 | 0.5 | 4.7 |
| Ketoprofen | 1.9 | 0.25 | 5.9 |
| Indomethacin | 1.5 | 0.5 | 4.2 |

These tests employed for measuring the in vivo activities of the compounds of the present invention are modifications of the methods described in the following literature and are as follows:

(1) The Carrageenin-induced Rat Paw Edema Test

Groups of 6 to 10 male Wistar rats weighing 170 to 200 g were used. According to the method of Winter et al., Proc. Soc. Exp. Biol. Med., 111, 544 (1962), 0.05 ml of 1% carrageenin solution was injected into the foot pad of right hind paw. The test compound was suspended in 5% gum arabic solution and orally given one hour before the carrageenin injection. Control rats received only gum arabic. Foot volume was determined with a plethysmometer 4 hours after the carrageenin injection. Edema volume was calculated by subtracting the volume of the left foot from the right one. The dose which gave 30% reduction of edema volume from that of the control group, $ED_{30}$, was calculated.

(2) The Adjuvant-induced Arthritis Test

According to the method of Winter et al., Arth. Rheum., 9, 394 (1966), groups of 20 male Sprague-Dawley rats weighing 160 to 180 g were given subplantar injection of the adjuvant consisting of 0.5 mg of killed *Mycobacterium butyricum* (Difco) and 0.1 ml of liquid paraffin. Fourteen days after, the rats with established arthritis were treated by the drug as follows: The test compound was suspended in 5% gum arabic solution and orally given once a day for 5 days, day 15 to day 19. Control rats were given gum arabic in the same way. On day 19, the volume of right foot was determined with a plethysmometer. The lowest dose which gave significant reduction (p<0.001) of the foot volume from that of the control group was regarded as a minimum effective dose (MED).

(3) The Ulceration of Rat Small Intestine Test

Groups of 6 male Wistar rats were orally given the test compound suspended in 5% gum arabic solution. After 24 hrs, the lesions in the small intestine were detected by the modified method of Brodie et al., Science 170, 184 (1970). The rats were given intravenously 1 ml of 2.5% pontamine sky blue in physiological saline solution, and 10 minutes later, they were killed by decapitation. Small intenstines were excised, thoroughly washed with a saline solution and fixed in 75% ethanol. They were then immersed in ethanol containing 5% $H_2O_2$ for 10 min in order to decolorize hemoglobin, washed with ethanol to remove $H_2O_2$ and stored in ethanol. The degree of ulceration was presented by ulcer index. Each one-cm long segment of the small intestine was graded for ulcer scroes; 0: none; 1: lesions less than 1 $mm^2$, 2: lesions from 1 $mm^2$ to 9 $mm^2$, 3: lesions more than 9 $mm^2$. All scores were summed up, and ulcer index was calculated by the following equation:

$$\text{Ulcer index } (U.I.) = \frac{\text{total score}}{\left(\begin{array}{c}\text{length of small}\\ \text{intestine in cm}\end{array}\right) \times 3} \times 100$$

Dose which resulted in ulceration with U.I. of more than 15 in 50% of animals, $UD_{50}$, was calculated by the method of Litchfield and Wilcoxon, J. Pharm. Exp. Ther., 96, 99 (1949).

These results highly suggest that the compounds of this invention may be effective in the treatment of such inflammatory diseases as rheumatoid arthritis, osteoarthritis, arthritis deformans and lumbago in mammals.

The compounds of this invention may be used in the form of pharmaceutical composition adapted for enteral or parenteral administration. Accordingly, said compounds can be combined with solid or liquid pharmaceutical carriers, and formulated in the form of tablets, capsules, powder packets, granules, suspensions, syrups, ointment, cream, jelly, suppositories, poultices, liquids, emulsions, injections and the like. The pharmaceutical preparation may also contain non-toxic auxiliary substances such as preservatives, stabilizers, wetting agents, detergents, buffers and the like. These pharmaceutical compositions containing the compound of the present invention as an active ingredient can be prepared according to the usual formulation methods.

In the treatment of inflammatory diseases in man, the compounds of this invention may generally be administered in an amount of from about 30 mg/kg/day to 1500 mg/kg/day depending upon the symptom, the route of administration, and the particular compound of the invention.

According to the present invention, the 5-substituted 1,2,4-oxadiazole derivatives of the aforesaid formula (I) can be prepared by the following various synthetic routes which are already described in literature.

Said processes comprise:

(a) reacting a carboxylic acid of the formula,

R—T—COOH          (II)

wherein R and T are as defined above, or its reactive ester, with an amidoxime of the formula,

(III)

wherein U is as defined above, to yield an O-acylamidoxime of the formula,

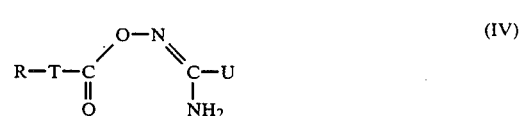

(IV)

wherein R, T and U are as defined above, and further effecting intramolecular condensation to produce a compound of the formula,

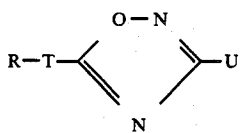 (I)

wherein R, T, and U are as defined above,
(b) reacting a nitrile of the formula,

 (V)

wherein R and T are as defined above, with a nitrile oxide of the formula,

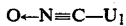 (VI)

wherein $U_1$ is lower alkyl, lower alkenyl, polyhalo-lower alkyl, lower cycloalkyl, lower cycloalkenyl, phenyl, substituted phenyl, pyridyl or a group of the formula $R_{16}$-$T_2$-[wherein $R_{16}$ is halogen, lower alkoxy, lower alkenyloxy, di-lower alkoxymethyl, carboxy, lower cycloalkyl, phenyl, substituted phenyl, pyridyl,

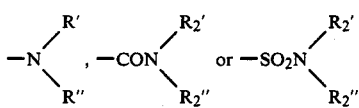

(wherein R', R'', $R_2'$ and $R_2''$ are as defined above); and $T_2$ is lower alkylene or lower alkenylene], to yield a compound of the formula,

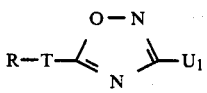 (Ia)

wherein R, T and $U_1$ are as defined above,
(c) reacting a thioamide derivative of the formula,

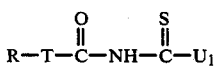 (VII)

wherein R, T and $U_1$ are as defined above, with hydroxylamine to yield a compound of the aforesaid formula (Ia),
(d) reacting an aldehyde of the formula,

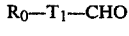 (VIII)

wherein $R_0$ is the same as R provided that $X_1$, $X_2$ and $X_3$ in the definition R are not the radical —S—; and $T_1$ is as defined above, with an amidoxime of the formula,

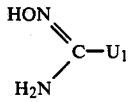 (IIIa)

wherein $U_1$ is as defined above, to yield a compound of the formula,

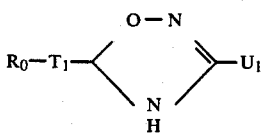 (Ib)

wherein $R_0$, $T_1$ and $U_1$ are as defined above, and further oxidizing it to produce a compound of the formula,

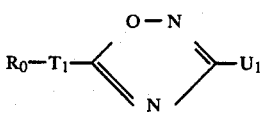 (Ic)

wherein $R_0$, $T_1$ and $U_1$ are as defined above,
(e) reacting a compound of the formula,

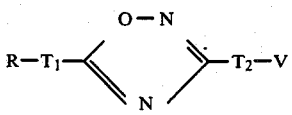 (Id)

wherein R, $T_1$ and $T_2$ are as defined above, and V is a radical that affords —O—, —S—, —NH— or

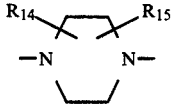

wherein $R_{14}$ and $R_{15}$ are as defined above) on the reaction with the radical W of a compound of the formula, $R_{13}$—W (IX)

wherein $R_{13}$ is as defined above, and W is a radical that affords —O—, —S—, —NH— or

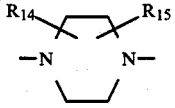

(wherein $R_{14}$ and $R_{15}$ are as defined above) on the reaction with the aforesaid radical V, with said compound (IX), to yield a compound of the formula,

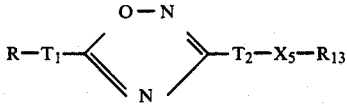 (Ie)

wherein R, $R_{13}$, $T_1$ and $T_2$ are as defined above; and $X_5$ is —O—, —S—, —NH—

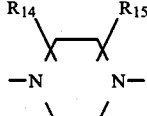

(wherein $R_{14}$ and $R_{15}$ are as defined above,
(f) reacting an alcohol compound of the formula,

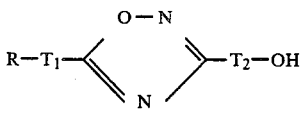 (If)

or its reactive ester wherein R, $T_1$ and $T_2$ are as defined above, with a compound of the formula, $R_{17}$—H  (X)

wherein $R_{17}$ is sulfo, cyano, or the group

(wherein R' and R" are as defined above, provided that this amino group is not a quaternary ammonium salt or N-oxide), or a salt of said compound (X), to yield a compound of the formula,

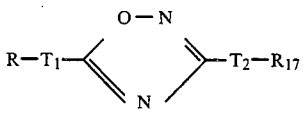 (Ig)

wherein R, $R_{17}$, $T_1$ and $T_2$ are as defined above, and
(g) hydrolyzing a compound of the formula,

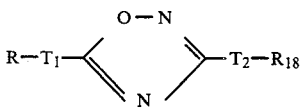 (Ih)

wherein R, $T_1$ and $T_2$ are as defined above, and $R_{18}$ is cyano, lower alkoxycarbonyl, di-lower alkoxymethyl, acylamino, acyloxy, acylthio or tetrahydropyranyloxy, to yield a compound of the formula,

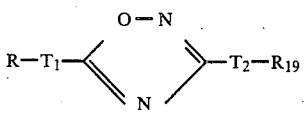 (Ii)

wherein R, $T_1$ and $T_2$ are as defined above, and $R_{19}$ is carboxy, formyl, amino, hydroxy or mercapto.

To produce the compounds of this invention of the formula (I), it is also useful to employ the other known art (cf. A. R. Katritzky and A. J. Boulton (Ed.)), "Advances in Heterocyclic Chemistry", Vol. 20, pp. 65–116 (1976)) and the conventional methods for the conversion of the functional groups in organic chemistry.

The above-mentioned methods for preparing the compounds of this invention will be explained in detail below.

In the method (a), a carboxylic acid or its reactive ester of the aforesaid formula (II) is reacted with an amidoxime of the formula (III) in an inert solvent above or below room temperature. As the reactive ester of the carboxylic acid, there may be preferably used a carboxylic acid halide such as chloride, bromide or iodide, a carboxylic acid anhydride including a mixed anhydride, a carboxylic azide or an activated ester such as 4-acyloxy-2,3-dihydro-2,5-diphenyl-3-oxothiophene 1,1-dioxide. The free acid may be preferably reacted in the presence of N,N'-dicyclohexylcarbodiimide (DCC), 1-hydroxybenzotriazole-DCC, N,N'-carbonyldiimidazole or the like. Suitable solvents include, for example, benzene, toluene, xylene, dichloromethane, chloroform, dichloroethane, trichloroethane, diethyl ether, tetrahydrofuran (THF), dioxane, dimethoxyethane, pyridine, dimethylformamide (DMF) and the like. The acid halide or anhydride may be preferably reacted in the presence of the basic condensing agent including inorganic and organic bases, e.g., sodium hydroxide, potassium hydroxide, sodium carbonate, potassium carbonate, triethylamine, N,N-dimethylaniline, pyridine and the like. In case the intermediate 0-acylamidoxime of the aforesaid formula (IV) is isolated in this reaction, it can be converted to the desired compound (I) via dehydrating-intramolecular cyclization with further heating in the presence or absence of an inert solvent.

In the method (b), a nitrile of the aforesaid formula (V) is reacted with a nitrile oxide of the formula (VI) in an inert solvent. The nitrile compound may be generally employed in a proportion of 2 to 5 moles per mole of the nitrile oxide, but in the case of liquid nitrile, a great excess of the nitrile is conveniently used as a reaction solvent.

Suitable solvents for the above process step include diethyl ether, tetrahydrofuran, dimethoxyethane, and the like. The reaction may be easily effected at room temperature, if necessary, above or below room temperature depending upon reactivity of the reactants employed. Use of Lewis acid catalysts such as boron trifluoride may be effective.

In the method (c), a thioamide derivative of the aforesaid formula (VII) is reacted in an inert solvent with an excess of hydroxylamine in the presence of a base. Suitable solvents are ethanol, n-propyl alcohol, isopropyl alcohol, n-butyl alcohol, dioxane, pyridine and the like. This reaction step is conveniently carried out by using 2–5 molar equivalents of hydroxylamine hydrochloride with a base such as triethylamine, pyridine, potassium carbonate, sodium acetate and the like. It is preferably conducted at a temperature between room temperature and the boiling point of the reaction mixture.

In the method (d), an aldehyde of the aforesaid formula (VIII) is first reacted with an amidoxime of the formula (IIIa) with heating to yield a 4,5-dihydro-1,2,4-oxadiazole derivative of the formula (Ib). This condensation reaction is preferably effected in a solvent such as an alcohol, e.g., methanol, ethanol, isopropyl alcohol, n-butyl alcohol, tert-butyl alcohol or the like, at a temperature within the range of from room temperature to reflux temperature. In the next process step, the intermediate compound (Ib) may be converted to the oxadiazole derivative of the aforesaid formula (Ic) by oxidation in an inert solvent with an oxidizing agent. Suitable oxidizing agents are potassium permanganate, manganese dioxide, chromium trioxide, sodium metaperiodate, sodium hypochlorite and the like. Solvents suitable for this process step include, for example, acetic acid, water, methanol, ethanol, isopropyl alcohol, tetrahydrofuran, dioxane, chloroform, benzene, toluene and a mixture thereof. The solvent may be chosen depending on the oxidizing agent employed.

In the method (e), a compound of the aforesaid formula (Id) is reacted in an inert solvent with a compound of the formula (IX) with or without a base above or below room temperature. One of the symbol V of the formula (Id) and the symbol W of the formula (IX) means a radical selected from the group consisting of hydroxy, mercapto, amino and

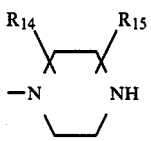

(wherein $R_{14}$ and $R_{15}$ are as defined above), and the other means a radical selected from the group consisting of chloro, bromo, iodo, acyloxy, benzenesulfonyloxy, p-toluenesulfonyloxy, methanesulfonyloxy, and trichloromethanesulfonyloxy. In general, V and W are suitably chosen depending on both the objective compound (Ie) and the available reactant (IX). Solvents which may be utilized include ethers, e.g., diethyl ether, tetrahydrofuran, dioxane, diethyleneglycol dimethyl ether, etc.; hydrocarbon solvents, e.g., benzene, toluene, xylene, etc.; ketone solvents, e.g., acetone, methyl ethyl ketone, methyl isobutyl ketone, etc.; alcohols, e.g., methanol, ethanol, isopropyl alcohol, etc.; dimethylformamide, dimethylacetamide, dimethylsulfoxide, water and a mixture thereof. Suitable bases include sodium hydroxide, potassium hydroxide, sodium carbonate, potassium carbonate, metallic sodium, sodium hydride, sodium methoxide, sodium ethoxide, triethylamine, N,N-dimethylaniline, pyridine and the like.

In the method (f), an alcohol compound of the aforesaid formula (If) or its reactive ester is reacted in an inert solvent with a compound of the formula (X) or its salt around room temperature or higher under basic or neutral conditions. Suitable reactive esters of the alcohol (If) include, for example, chloride, bromide, iodide, p-toluenesulfonate, methanesulfonate and trichloromethanesulfonate. Examples of the compound of the formula (X) or its salt for this process step include sodium cyanide, potassium cyanide, sodium sulfite, ammonia, dimethylamine, diethylamine, diethanolamine, pyrrolidine, piperidine, morpholine, pyrrole, pyrazole, imidazole and the like. Suitable solvents include, for example, alcohols, e.g., methanol, ethanol, isopropyl alcohol, n-butyl alcohol, etc.; ketones, e.g., acetone, methyl isobutyl ketone, etc.; tetrahydrofuran; dioxane; acetonitrile; dimethylformamide; dimethylsulfoxide; water; and a mixture thereof.

In the method (g), a compound of the aforesaid formula (Ih) is hydrolyzed in an inert solvent by treatment with an acid or a base around room temperature or higher. Solvents which may be utilized include alcohols, e.g., methanol, ethanol, isopropyl alcohol, n-butyl alcohol, ethyleneglycol, etc.; ketones, e.g., acetone, methyl ethyl ketone, methyl isobutyl ketone, etc.; dioxane; acetic acid; water; benzene; toluene; and the like. This hydrolysis is suitably effected in the presence of a base such as sodium hydroxide, potassium hydroxide, potassium carbonate, ammonia water or the like, or in the presence of an acid such as hydrochloric acid, hydrobromic acid, sulfuric acid, phosphoric acid, methanesulfonic acid, acetic acid, pyridine hydrochloride or the like.

The quaternary ammonium salt of the formula

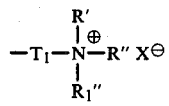

and the sulfonium salt of the formula

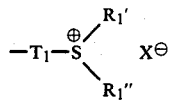

(wherein R', R", $R_1'$, $R_1''$, $T_1$ and X are as defined above) can conveniently be prepared by reacting a tertiary amine of the formula

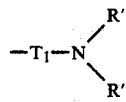

or a sulfide of the formula $-T_1-S-R_1'$ (wherein R', R", $R_1'$ and $T_1$ are as defined above) with an euqimolar or excess of the compound of the formula $R_1''-X$ (wherein $R_1''$ and X are as defined above). The reaction is preferably carried out in the presence or absence of an inert solvent at temperatures below or above room temperature. Suitable solvents are methanol, ethanol, n-propyl alcohol, n-butyl alcohol, acetonitrile, nitromethane, methylene chloride, chloroform, carbon tetrachloride, benzene, toluene, xylene, diethyl ether, diisopropyl ether, acetone, dimethylformamide and the like.

The amidoximes and nitrile oxides which are the important starting compounds of this invention may be prepared by the procedures reported in literature (see, for example, F. Eloyl et al., Chemical Review, 62, 155 (1962) and A. R. Katritzky et al. (ed.) "Advances in Heterocyclic Chemistry", Vol. 20, page 65).

The following Examples are given by way of illustration and are not to be construed as limitation of this invention.

EXAMPLE 1

To a suspension of 2.44 g of 2-(2-fluoro-4-biphenylyl)-propionic acid (flurbiprofen) in 50 ml of dry benzene was added 2.38 g of thionyl chloride. The mixture was heated under reflux with stirring for 2 hours and then concentrated to dryness under reduced pressure. The residue was dissolved in 5 ml of dry benzene and the solution was added dropwise with ice-cooling to a solution of 0.815 g of acetamidoxime in 20 ml of dry pyridine. The resultant mixture was stirred at room temperature for 30 minutes and heated under reflux for 5 hours. After evaporating the solvent under reduced pressure, the mixture was partitioned between 100 ml of benzene and 20 ml of 10% sodium carbonate solution. The organic phase was washed with water, dried over sodium sulfate and evaporated. The residue was chromatographed over silica gel using benzene as an eluent to give 1.7 g of 5-(3-fluoro-4-phenyl-α-methylbenzyl)-3-methyl-1,2,4-oxadiazole as a colorless oil. It was crystallized from n-hexane to give colorless needles, m.p. 55°–56° C.

EXAMPLE 2

To a mixture of 4.34 g of chloroacetamidoxime and 4.08 g of triethylamine in 150 ml of dry tetrahydrofuran (THF) was added dropwise at −10° to 0° C. a solution in 15 ml of THF of the acid chloride which was prepared from 9.77 g of flurbiprofen as described in Example 1. After stirring for 2 hours at room temperature, the reaction mixture was diluted with aqueous sodium bicarbonate solution and extracted with benzene. The organic phase was washed with water, dried over sodium sulfate and evaporated to give 12.3 g of crude 0-[2-(2-fluoro-4-biphenylyl)propionyl]-chloroacetamidoxime as a brown oil.

After dissolving this material in 200 ml of toluene, the solution was heated under reflux for 10 hours and concentrated to dryness under reduced pressure. The residue was chromatographed over silica gel using benzene. Crystallization of the clean fractions from diisopropyl ether yielded 9.25 g of 3-chloromethyl-5-(3-fluoro-4-phenyl-α-methylbenzyl)-1,2,4-oxadiazole as colorless needles, m.p. 98°–99° C.

EXAMPLE 3

To a solution of 3.81 g of 4-(4-biphenylyl)-4-oxobutyric acid (fenbufen) and 1.52 g of triethylamine in 90 ml of dry THF was added dropwise 1.63 g of ethyl chlorocarbonate and then added 1.63 g of chloroacetamidoxime in 10 ml of dry THF at −5° to 0° C. After stirring for 6 hours at room temperature, the reaction mixture was diluted with ice-water and made basic by addition of sodium bicarbonate solution. The precipitated material was collected by filtration, washed with water and dried to give 4.7 g of 0-[4-(4-biphenylyl)-4-oxobutyryl]chloroacetamidoxime as colorless fine crystals.

A suspension of this material in 300 ml of xylene was heated with stirring under reflux for 8 hours and then evaporated. The residue was chromatographed over silica gel using chloroform to give 3.65 g of 5-[3-(4-biphenylyl)-3-oxopropyl]-3-chloromethyl-1,2,4-oxadiazole. It was recrystallized from ethyl acetate to give colorless needles, m.p. 153°–153.5° C.

EXAMPLE 4

To a mixture of 2.8 g of 2-(2,6-dichloroanilino)-phenylacetic acid (dichlofenac), 0.70 g of acetamidoxime and 1.28 g of 1-hydroxybenzotriazole and 50 ml of dimethylformamide (DMF) was added with ice-cooling 2.15 g of N,N'-dicyclohexylcarbodiimide, and the resultant mixture was then stirred at room temperature overnight. The reaction mixture was diluted with ice-water, made basic by addition of sodium bicarbonate solution, and extracted with ethyl acetate. After removing the precipitated material by filtration, the organic phase was washed successively with sodium bicarbonate solution and water, dried over sodium sulfate and evaporated to give 3.2 g of crude 0-[2-(2,6-dichloanilino)benzyl]acetamidoxime as a brown oil.

A suspension of this material in 150 ml of xylene was heated under reflux for 3 hours and then evaporated. The residue was chromatographed over silica gel using benzene. The combined clean fractions were crystallized from diisopropyl ether to give 1.86 g of 5-[2-(2,6-dichloroanilino)benzyl]-3-methyl-1,2,4-oxadiazole as colorless needles, m.p. 93.5°–94.5° C.

EXAMPLES 5 to 22

According to substantially the same procedure as that of Example 1, there were obtained the 1,2,4-oxadiazole derivatives of the formula (I) as listed in Table II.

TABLE II

| Example No. | R—T— | U | Physical Data |
| --- | --- | --- | --- |
| 5 | 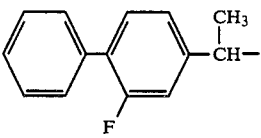 | 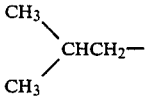 | m.p. 101.5–102° C. |
| 6 | " | 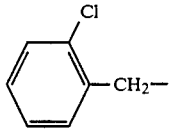 | $n_D^{23}$ 1.5963 |
| 7 | " | 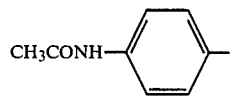 | m.p. 128–129° C. |
| 8 | " | 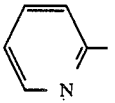 | m.p. 101.5–102° C. |
| 9 | 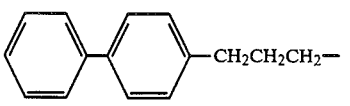 | —CH$_3$ | $n_D^{26}$ 1.5822 |

TABLE II-continued

| Example No. | R—T— | U | Physical Data |
|---|---|---|---|
| 10 | 2-F-C6H4-C(O)-C6H4-CH2CH2CH2CH2— | " | $n_D^{24}$ 1.5643 |
| 11 | C6H5-C(O)-C6H4-CH(CH3)— (meta) | " | $n_D^{18}$ 1.5844 |
| 12 | C6H5-O-C6H4-CH(CH3)— (meta) | " | $n_D^{24}$ 1.5649 |
| 13 | C6H5-CH2-C6H4-CH(CH3)— (meta) | " | $n_D^{18}$ 1.5650 |
| 14 | C6H5-C(O)-C6H4-CH(CH3)— (meta) | (CH3)2CHCH2— | $n_D^{16}$ 1.5620 |
| 15 | 2-thienyl-C(O)-C6H4-CH(CH3)— | —CH3 | $n_D^{25}$ 1.6057 |
| 16 | phthalimidinyl-C6H4-CH(CH3)— | " | m.p. 159–160° C. (decomp.) |
| 17 | 5-chloro-6-cyclohexyl-indanyl— | " | $n_D^{18}$ 1.5610 |
| 18 | 5-methoxy-2-methyl-1-(4-chlorobenzoyl)-indol-3-yl-CH2— | " | m.p. 110–111° C. |
| 19 | 2-oxocyclopentyl-CH2-C6H4-CH(CH3)— | " | $n_D^{20}$ 1.5340 |

TABLE II-continued

| Example No. | R—T— | U | Physical Data |
|---|---|---|---|
| 20 | 4-Cl-C6H4-benzoxazol-5-yl-CH(CH3)— | " | m.p. 136.5–137.5° C. |
| 21 | 2-fluoro-biphenyl-4-yl-C(CH3)=CH— | " | m.p. 110.5–111° C. |
| 22 | 2-fluoro-biphenyl-4-yl-CH(CH3)— | cyclopropyl | $n_D^{28}$ 1.5730 |

EXAMPLES 23 to 27

According to substantially the same procedure as that of Example 2, there were obtained the 1,2,4-oxadiazole derivatives of the formula (I) as listed in Table III.

EXAMPLES 28 to 32

According to substantially the same procedure as that of Example 3, there were obtained the 1,2,4-oxadiazole derivatives of the formula (I) as listed in Table IV.

TABLE III

| Example No. | R—T— | U | Physical Data |
|---|---|---|---|
| 23 | 2-fluoro-biphenyl-4-yl-CH(CH3)— | H | m.p. 58–59° C. |
| 24 | 3-benzoyl-phenyl-CH(CH3)— | H | $n_D^{14}$ 1.5970 |
| 25 | [2-(phenyl-C(=N)-S-)-1-(4-Cl-C6H4)-propenyl]-CH2— | —CH3 | m.p. 113–114° C. |
| 26 | [5-fluoro-3-methyl-1-(4-methylsulfinyl-benzylidene)-indenyl]-CH2— | —CH3 | m.p. 127–128.5° C. |
| 27 | 2-chloro-4-(allyloxy)-benzyl- | —CH2Cl | $n_D^{20}$ 1.5663 |

TABLE IV

| Example No. | R—T— | U | Physical Data |
|---|---|---|---|
| 28 | 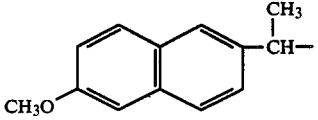 | —CH₃ | m.p. 104–104.5° C. |
| 29 | 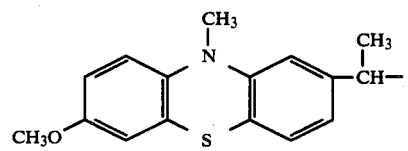 | " | $n_D^{26}$ 1.6358 |
| 30 | 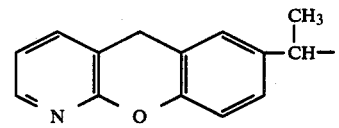 | " | m.p. 119–120° C. |
| 31 | 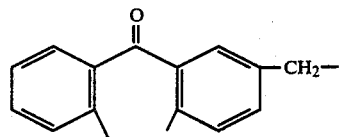 | " | m.p. 117.5–118.5° C. |
| 32 | 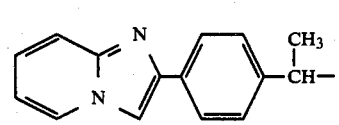 | " | m.p. 128–129° C. |

EXAMPLES 33 to 34

According to substantially the same procedure as that of Example 4, there were obtained the 1,2,4-oxadiazole derivatives of the formula (I) as listed in Table V.

TABLE V

| Example No. | R—T— | U | Physical Data |
|---|---|---|---|
| 33 | 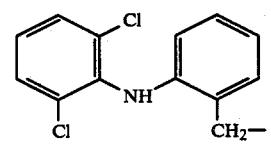 | —CH₂Cl | m.p. 125.5–126.5° C. |
| 34 | 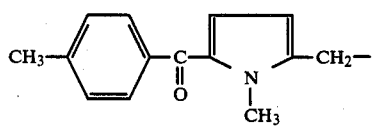 | CH₃ | m.p. 126–126.5° C. |

EXAMPLE 35

According to substantially the same procedure as that of Example 2, there were obtained the following 1,2,4-oxadiazole derivatives:

5-[1-(4-Chlorobenzyoyl)-5-methoxy-2-methylindol-3-ylmethyl]-3-isobutyl-1,2,4-oxadiazole, IR $v_{max}^{neat}$ cm⁻¹: 1690, 1580, 1480, 1370, 1320, 760.

5-[1-(4-Chlorobenzoyl)-5-methoxy-2-methylindol-3-ylmethyl]-3-isopropyl-1,2,4-oxadiazole, m.p. 93°–94° C.

5-[1-(4-Chlorobenzoyl)-5-methoxy-2-methylindol-3-ylmethyl]-3-(n-propyl)-1,2,4-oxadiazole, m.p. 92.5°–93.5° C.

5-[1-(4-Chlorobenzoyl)-5-methoxy-2-methylindol-3-ylmethyl]-3-cyclopropyl-1,2,4-oxadiazole, m.p. 119°–120° C.

5-[1-(4-Chlorobenzoyl)-5-methoxy-2-methylindol-3-ylmethyl]-3-(3-methylthiopropyl)-1,2,4-oxadiazole, m.p. 87°–88° C.

5-[1-(4-Chlorobenzoyl)-5-methoxy-2-methylindol-3-ylmethyl]-3-methylthiomethyl-1,2,4-oxadiazole, IR $v_{max}^{neat}$ cm⁻¹: 1685, 1590, 1580, 1480, 1360, 1320, 760.

5-[1-(4-Chlorobenzoyl)-5-methoxy-2-methylindol-3-ylmethyl]-3-chloromethyl-1,2,4-oxadiazole, m.p. 101°–102° C.

5-[3-Chloro-4-(pyrrol-1-yl)-α-methylbenzyl]-3-methyl-1,2,4-oxadiazole, $n_D^{23}$ 1.5787

5-[4-(Benzothiazol-2-yl)benzyl]-3-methyl-1,2,4-oxadiazole, m.p. 109°–109.5° C.

EXAMPLE 36

According to substantially the same procedure as that of Example 4, there were obtained the following 1,2,4-oxadiazole derivatives:

5-[2-(2,6-Dichloroanilino)benzyl]-3-isobutyl-1,2,4-oxadiazole, m.p. 67.5°–69° C.

5-(3-Benzoyl-α-methylbenzyl)-3-isopropyl-1,2,4-oxadiazole, IR $\nu_{max}^{neat}$ cm$^{-1}$: 1665, 1580, 1320, 1285, 1260.

5-(3-Benzoyl-α-methylbenzyl)-3-ethyl-1,2,4-oxadiazole, IR $\nu_{max}^{neat}$ cm$^{-1}$: 1665, 1600, 1580, 1450, 1385.

5-[2-(2,3-Dimethylanilino)phenyl]-3-methyl-1,2,4-oxadiazole, m.p. 146.5°–147° C.

5-[1-(4-Chlorobenzoyl)-5-methoxy-2-methylindol-3-ylmethyl]-3-(pyrrol-1-ylmethyl)-1,2,4-oxadiazole, m.p. 113.5°–114.5° C.

EXAMPLE 37

To a suspension of 950 mg of 2-(2-fluoro-4-biphenylyl)propionic acid in 20 ml of dry benzene was added 2 ml of thionyl chloride. The mixture was heated under reflux for 2 hours and then concentrated to dryness under reduced pressure. The residue was dissolved in 18 ml of diethyl ether and the solution was added dropwise with ice-cooling to a solution of 600 mg of trifluoroacetamidoxime and 400 mg of triethylamine. After stirring for 2 hours, the reaction mixture was filtered, and the filtrate was evaporated under reduced pressure. The residue was heated at about 100° C. for 1 hour and then chromatographed over silica gel using n-hexane-chloroform (1:1, v/v) to yield 500 mg of 5-(3-fluoro-4-phenyl-α-methylbenzyl)-3-trifluoromethyl-1,2,4-oxadiazole as a colorless oil, $n_D^{19}$ 1.5304.

EXAMPLE 38

To a solution of 3.82 g of 3-chloromethyl-5-(3-fluoro-4-phenyl-α-methylbenzyl)-1,2,4-oxadiazole in 50 ml of dimethyl sulfoxide (DMSO) was added 0.75 g of sodium cyanide. After stirring for 1 hour at room temperature, the reaction mixture was poured into ice-water. The resultant mixture was extracted with benzene and the extracts were washed with water, dried over sodium sulfate and evaporated. The residue was chromatographed over silica gel using benzene to yield 2.4 g of 3-cyanomethyl-5-(3-fluoro-4-phenyl-α-methylbenzyl)-1,2,4-oxadiazole. It was recrystallized from ethyl acetate-diisopropyl ether to give colorless plates, m.p. 111°–112° C.

EXAMPLE 39

To a solution of 1.4 g of 3-cyanomethyl-5-(3-fluoro-4-phenyl-α-methylbenzyl)-1,2,4-oxadiazole obtained in Example 38 in 50 ml of methanol was added a solution of 2.56 g of potassium hydroxide in 23 g of water. After stirring under reflux for 4 hours, the reaction mixture was cooled, diluted with water and extracted with chloroform. The organic phase was washed with water, dried over sodium sulfate and evaporated. The residue was chromatographed over silica gel using chloroform-methanol (20:1, v/v) to give 1.35 g of 3-carboxymethyl-5-(3-fluoro-4-phenyl-α-methylbenzyl)-1,2,4-oxadiazole as an oil. It was crystallized from diisopropyl ether to give colorless fine needles, m.p. 100.5°–101.5° C.

EXAMPLE 40

To a solution of 1.27 g of 3-carboxymethyl-5-(3-fluoro-4-phenyl-α-methylbenzyl)-1,2,4-oxadiazole obtained in Example 39 in 20 ml of dry methanol was added a drop of conc. sulfuric acid. The mixture was allowed to stand at room temperature overnight and then concentrated to dryness under reduced pressure. The solution of the residue in benzene was washed successively with a sodium bicarbonate solution and water, dried over sodium sulfate and evaporated. The residue was chromatographed over silica gel using benzene to give 0.95 g of 3-methoxycarbonylmethyl-5-(3-fluoro-4-phenyl-α-methylbenzyl)-1,2,4-oxadiazole, $n_D^{25}$ 1.5618.

EXAMPLE 41

To a solution of 1.03 g of 5-[3-(4-biphenylyl)-3-oxopropyl]-3-chloromethyl-1,2,4-oxadiazole obtained in Example 3 in 100 ml of ethanol was added 0.12 g of sodium borohydride. After stirring for 10 minutes at room temperature, the reaction mixture was concentrated under reduced pressure. The residue was treated with ice-water and extracted with chloroform. The organic phase was washed with water, dried over sodium sulfate and evaporated to give 1.0 g of 5-[3-(4-biphenylyl)-3-hydroxypropyl]-3-chloromethyl-1,2,4-oxadiazole, m.p. 48°–49° C.

EXAMPLE 42

According to substantially the same procedure as that of Example 1, treatment of 5.38 g of 2-(2-fluoro-4-biphenylyl)propionic acid with 4.56 g of 3-tetrahydropyranyloxypropionamidoxime yielded 5-(3-fluoro-4-phenyl-α-methylbenzyl)-3-(2-tetrahydropyranyloxyethyl)-1,2,4-oxadiazole.

To a solution of this crude material in 100 ml of ethanol was added 40 ml of 2N-hydrochloric acid. The resultant mixture was stirred at room temperature for 1 hour, and then concentrated to dryness under reduced pressure. After the residue was neutralized by addition of 5% sodium hydroxide solution, the mixture was extracted with chloroform. The organic phase was washed with water, dried over sodium sulfate and evaporated. The residue was chromatographed over silica gel using chloroform to give 3.45 g of 5-(3-fluoro-4-phenyl-α-methylbenzyl)-3-(2-hydroxyethyl)-1,2,4-oxadiazole, $n_D^{26}$ 1.5772.

EXAMPLE 43

To a solution of 2.62 g of 5-(3-fluoro-4-phenyl-α-methylbenzyl)-3-(2-hydroxyethyl)-1,2,4-oxadiazole in 60 ml of dry benzene was successively added 2.0 g of thionyl chloride and 0.67 g of pyridine with ice-cooling. After stirring and heating with reflux for 1 hour, the reaction mixture was washed with water. The organic phase was further washed with water, dried over sodium sulfate and evaporated. The residue was chromatographed over silica gel using benzene to give 2.44 g of 3-(2-chloroethyl)-5-(3-fluoro-4-phenyl-α-methylbenzyl)-1,2,4-oxadiazole, m.p. 72°–72.5° C.

EXAMPLE 44

To a solution of 2.44 g of 3-(2-chloroethyl)-5-(3-fluoro-4-phenyl-α-methylbenzyl)-1,2,4-oxadiazole in 40 ml of DMF was added 1.69 g of potassium thioacetate. After stirring at room temperature overnight, the reaction mixture was poured into ice-water. The resultant mixture was extracted with benzene and the organic phase was washed with water, dried over sodium sulfate and evaporated under reduced pressure. The residue was chromatographed over silica gel using benzene to yield 2.62 g of 3-(2-acetylthioethyl)-5-(3-fluoro-4-phenyl-α-methylbenzyl)-1,2,4-oxadiazole as a light brown oil. It was crystallized from diisopropyl ether to give colorless needles, m.p. 56°–57° C.

EXAMPLE 45

To a solution of 1.59 g of 3-chloromethyl-5-(3-fluoro-4-phenyl-α-methylbenzyl)-1,2,4-oxadiazole, which was obtained by the method described in Example 2, in 30 ml of DMF was added 1.14 g of potassium thioacetate. After stirring for 3 hours at room temperature, the reaction mixture was poured into ice-water. The mixture was extracted with benzene and the organic phase was washed with water, dried over sodium sulfate and evaporated. The residue was chromatographed over silica gel using benzene to yield 1.75 g of 3-acetylthiomethyl-5-(3-fluoro-4-phenyl-α-methylbenzyl)-1,2,4-oxadiazole as a colorless oil, $n_D^{20}$ 1.5910.

EXAMPLE 46

According to substantially the same procedure as that of Example 45, there were obtained the following compounds from the corresponding 5-substituted 3-chloromethyl-1,2,4-oxadiazole derivatives:

3-Acetylthiomethyl-5-[3-(4-biphenylyl)-3-oxopropyl]-1,2,4-oxadiazole, m.p. 77°–78° C.

3-Acetylthiomethyl-5-(4-allyloxy-3-chlorobenzyl)-1,2,4-oxadiazole, $n_D^{25}$ 1.5663.

3-Acetylthiomethyl-5-[2-(2,6-dichloroanilino)benzyl]-1,2,4-oxadiazole, m.p. 89.5°–90° C.

EXAMPLE 47

A mixture of 1.90 g of 3-chloromethyl-5-(3-fluoro-4-phenyl-α-methylbenzyl)-1,2,4-oxadiazole obtained by the method of Example 2, 1.44 g of 30% methyl mercaptan solution in methanol, 0.54 g of sodium methoxide and 70 ml of dry methanol was stirred and refluxed for 1 hour. After cooling the reaction mixture was diluted with water and extracted with benzene. The extracts were washed with water, dried over sodium sulfate and evaporated. The residue was chromatographed over silica gel using benzene to give 1.83 g of 5-(3-fluoro-4-phenyl-α-methylbenzyl)-3-methylthiomethyl-1,2,4-oxadiazole as a colorless oil, m.p. 55.5°–56° C.

EXAMPLE 48

To a solution of 5.0 g of 3-(2-chloroethyl)-5-(3-fluoro-4-phenyl-α-methylbenzyl)-1,2,4-oxadiazole in 100 ml of ethanol was added 12.5 ml of 15% aqueous sodium methyl mercaptan. After stirring with reflux for 1 hour, the reaction mixture was concentrated under reduced pressure, diluted with water and extracted with ethyl acetate. The organic phase was washed with water, dried over magnesium sulfate and evaporated. The residue was chromatographed over silica gel using methylene chloride to give 4.78 g of 5-(3-fluoro-4-phenyl-α-methylbenzyl)-3-(2-methylthioethyl)-1,2,4-oxadiazole as a light yellow oil, $n_D^{21}$ 1.5860.

EXAMPLE 49

To a solution of 0.95 g of 5-(3-fluoro-4-phenyl-α-methylbenzyl)-3-methylthiomethyl-1,2,4-oxadiazole in 150 ml of ethanol was added a solution of 1.36 g of sodium metaperiodate in 50 ml of water. After stirring with reflux for 9 hours, the reaction mixture was cooled, diluted with water and extracted with chloroform. The extracts were washed with water, dried over sodium sulfate and evaporated under reduced pressure. The residue was chromatographed over silica gel using chloroform to yield 1.0 g of 5-(3-fluoro-4-phenyl-α-methylbenzyl)-3-methylsulfinylmethyl-1,2,4-oxadiazole. It was recrystallized from ethyl acetate-diisopropyl ether to give colorless needles, m.p. 71°–72° C. (decomp.).

EXAMPLE 50

To a solution of 1.59 g of 3-chloromethyl-5-(3-fluoro-4-phenyl-α-methylbenzyl)-1,2,4-oxadiazole in 70 ml of dry methanol was added 1.02 g of 28% sodium methoxide in methanol and 0.43 g of mercaptoethanol. After stirring for 2.5 hours at room temperature, the reaction mixture was diluted with water and extracted with benzene. The organic phase was washed with water, dried over sodium sulfate and evaporated. The residue was chromatographed over silica gel using chloroform to yield 1.75 g of 5-(3-fluoro-4-phenyl-α-methylbenzyl)-3-(2-hydroxyethylthiomethyl)-1,2,4-oxadiazole as a colorless oil, $n_D^{24}$ 1.5935.

EXAMPLE 51

According to substantially the same procedure as that described in Example 50 with the exception of using cysteamine instead of mercaptoethanol, there were obtained the following compounds from the corresponding 3-chloromethyl-1,2,4-oxadiazole derivatives:

3-(2-Aminoethylthiomethyl)-5-(3-fluoro-4-phenyl-α-methylbenzyl)-1,2,4-oxadiazole, $n_D^{21}$ 1.5945.

3-(2-(Aminoethylthiomethyl)-5-(3-benzoyl-α-methylbenzyl)-1,2,4-oxadiazole, IR $\nu_{max}^{neat}$ cm$^{-1}$: 1655, 1595, 1570, 1425, 1360, 1320, 1280.

EXAMPLE 52

To a solution of 1.32 g of 3-chloromethyl-5-(3-fluoro-4-phenyl-α-methylbenzyl)-1,2,4-oxadiazole in 30 ml of dry DMF was added 1.58 g of potassium acetate. After stirring at room temperature overnight, the reaction mixture was diluted with water and extracted with benzene. The organic phase was washed with water, dried over sodium sulfate and evaporated. The residue was chromatographed over silica gel using benzene to yield 0.96 g of 3-acetoxymethyl-5-(3-fluoro-4-phenyl-α-methylbenzyl)-1,2,4-oxadiazole, $n_D^{23}$ 1.5635.

EXAMPLE 53

According to substantially the same procedure as that of Example 42, there was obtained 3-(2-hydroxyethyl)-5-(4-isobutyl-α-methylbenzyl)-1,2,4-oxadiazole as a colorless oil ($n_D^{18}$ 1.5213) from 2-(4-isobutylphenyl)propionic acid.

EXAMPLE 54

According to the same procedure as that described in Example 2, there was obtained 5.5 g of 5-(4-biphenylylmethyl)-3-(2-tetrahydropyranyloxyethyl)-1,2,4-oxadiazole by the reaction of 3.19 g of 4-biphenylylacetic acid with 2.82 g of 3-tetrahydropyranyloxypropionamidoxime.

This material was dissolved in 100 ml of ethanol and to the solution was added 40 ml of 3N hydrochloric acid. After stirring for 1 hour at room temperature, the mixture was diluted with water and extracted with chloroform. The extracts were washed with water, dried over sodium sulfate and evaporated. The residual solid was recrystallized from ethyl acetate-diisopropyl ether to give 5-(4-biphenylylmethyl)-3-(2-hydroxyethyl)-1,2,4-oxadiazole, m.p. 94°–95° C.

EXAMPLE 55

According to substantially the same procedure as that of Example 42, there were obtained the following 3-(2-hydroxyethyl)-1,2,4-oxadiazole derivatives from the corresponding carboxylic acids:

5-(3-Benzoyl-α-methylbenzyl)-3-(2-hydroxyethyl)-1,2,4-oxadiazole, $n_D^{19}$ 1.5885.

5-(6-Chloro-5-cyclohexyl-1-indanyl)-3-(2-hydroxyethyl)-1,2,4-oxadiazole, $n_D^{19}$ 1.5645.

5-[1-(4-Chlorobenzoyl)-5-methoxy-2-methylindol-3-ylmethyl]-3-(2-hydroxyethyl)-1,2,4-oxadiazole, m.p. 113°–114° C.

EXAMPLE 56

According to substantially the same procedures as those of Examples 43 and 44, there were obtained the following compounds from the corresponding 5-substituted 3-(2-hydroxyethyl)-1,2,4-oxadiazole derivatives:

3-(2-Acetylthioethyl)-5-(4-isobutyl-α-methylbenzyl)-1,2,4-oxadiazole, $n_D^{23}$ 1.5299.

3-(2-Acetylthioethyl)-5-(4-biphenylylmethyl)-1,2,4-oxadiazole, m.p. 45.5°–46.5° C.

3-(2-Acetylthioethyl)-5-(6-chloro-5-cyclohexyl-1-indanyl)-1,2,4-oxadiazole, $n_D^{24}$ 1.5655.

3-(2-Acetylthioethyl)-5-(3-benzoyl-α-methylbenzyl)-1,2,4-oxadiazole, IR $\nu_{max}^{neat}$ cm$^{-1}$: 1690, 1660, 1595, 1575.

3-(2-Acetylthioethyl)-5-[1-(4-chlorobenzoyl)-5-methoxy-2-methylindol-3-ylmethyl]-1,2,4-oxadiazole, m.p. 113.5°–114° C.

EXAMPLE 57

To a solution of 1.56 g of 5-(3-fluoro-4-phenyl-α-methylbenzyl)-3-(2-hydroxyethyl)-1,2,4-oxadiazole in 40 ml of dry THF were successively added dropwise 0.56 g of triethylamine and 0.43 g of acetyl chloride with ice-cooling. After stirring for 4 hours at room temperature, the reaction mixture was poured into ice-water and extracted with benzene. The organic phase was washed with sodium bicarbonate solution, dried over sodium sulfate and evaporated under reduced pressure. The residue was chromatographed over silica gel using chloroform to give 1.57 g of 3-(2-acetoxyethyl)-5-(3-fluoro-4-phenyl-α-methylbenzyl)-1,2,4-oxadiazole as a colorless oil, $n_D^{23}$ 1.5564.

EXAMPLE 58

According to substantially the same procedure as that of Example 57, there was obtained 3-(2-acetoxyethylthiomethyl)-5-(3-fluoro-4-phenyl-α-methylbenzyl)-1,2,4-oxadiazole as a colorless oil having $n_D^{23}$ 1.5783 from 5-(3-fluoro-4-phenyl-α-methylbenzyl)-3-(2-hydroxyethylthiomethyl)-1,2,4-oxadiazole.

EXAMPLE 59

According to substantially the same procedure as that of Example 57, there were obtained the following compounds from the corresponding 3-(2-aminoethylthiomethyl)-1,2,4-oxadiazole derivatives:

3-[2-(N-Acetylamino)ethylthiomethyl]-5-(3-fluoro-4-phenyl-α-methylbenzyl)-1,2,4-oxadiazole, $n_D^{21}$ 1.5800.

3-[2-(N-Acetylamino)ethylthiomethyl]-5-(3-benzoyl-α-methylbenzyl)-1,2,4-oxadiazole, IR $\nu_{max}^{neat}$ cm$^{-1}$: 1660, 1570, 1285, 1215.

EXAMPLE 60

According to substantially the same procedure as that of Example 57, there was obtained 3-(4-acetylpiperazino)methyl-5-[1-(4-chlorobenzoyl)-5-methoxy-2-methylindol-3-ylmethyl]-1,2,4-oxadiazole (IR $\nu_{max}^{neat}$ cm$^{-1}$: 1690, 1640, 1580, 1480, 1460) from 5-[1-(4-chlorobenzoyl)-5-methoxy-2-methylindol-3-ylmethyl]-3-piperazinomethyl-1,2,4-oxadiazole.

EXAMPLE 61

To a solution of 1.52 g of 3-chloromethyl-5-(3-fluoro-4-phenyl-α-methylbenzyl)-1,2,4-oxadiazole in 30 ml of DMF was added 1.68 g of morpholine. The mixture was allowed to stand at room temperature overnight, then poured into ice-water and extracted with benzene. The organic phase was washed with water, dried over sodium sulfate and evaporated. The residue was chromatographed over silica gel using benzene-ethyl acetate (5:2, v/v) as an eluent to yield 1.83 g of 5-(3-fluoro-4-phenyl-α-methylbenzyl)-3-morpholinomethyl-1,2,4-oxadiazole as an oil. It was crystallized from diisopropyl ether to give colorless needles, m.p. 91.5°–92.5° C.

EXAMPLE 62

According to substantially the same procedure as that of Example 61, there were obtained the following compounds:

3-Dimethylaminomethyl-5-(3-fluoro-4-phenyl-α-methylbenzyl)-1,2,4-oxadiazole, $n_D^{25}$ 1.5621.

3-[Di-(2-hydroxyethyl)aminomethyl]-5-(3-fluoro-4-phenyl-α-methylbenzyl)-1,2,4-oxadiazole, $n_D^{17}$ 1.5741.

5-(3-Fluoro-4-phenyl-α-methylbenzyl)-3-isopropylaminomethyl-1,2,4-oxadiazole hydrochloride, m.p. 156.5°–157° C.

5-(3-Fluoro-4-phenyl-α-methylbenzyl)-3-pyrrolidinomethyl-1,2,4-oxadiazole, $n_D^{17}$ 1.5752.

3-Piperidinomethyl-5-(3-fluoro-4-phenyl-α-methylbenzyl)-1,2,4-oxadiazole, $n_D^{17}$ 1.5718.

5-(3-Fluoro-4-phenyl-α-methylbenzyl)-3-(4-methylpiperazinomethyl)-1,2,4-oxadiazole, $n_D^{17}$ 1.5693.

5-(3-Fluoro-4-phenyl-α-methylbenzyl)-3-[2,5-dimethyl-4-(3-phenylpropyl)piperazinomethyl]-1,2,4-oxadiazole, IR $\nu_{max}^{neat}$ cm$^{-1}$: 1570, 1485, 1455, 1420, 1380.

5-[1-(4-Chlorobenzoyl)-5-methoxy-2-methylindol-3-ylmethyl]-3-morpholinomethyl-1,2,4-oxadiazole, m.p. 111°–112° C.

5-[1-(4-Chlorobenzoyl)-5-methoxy-2-methylindol-3-ylmethyl]-3-piperazinomethyl-1,2,4-oxadiazole citrate, m.p. 147° C. (decomp.).

5-[1-(4-Chlorobenzoyl)-5-methoxy-2-methylindol-3-ylmethyl]-3-[4-(2-hydroxyethyl)-piperazinomethyl]-1,2,4-oxadiazole, IR $\nu_{max}^{neat}$ cm$^{-1}$: 3350–3400, 1720, 1600, 1580, 1490, 1460.

5-[1-(4-Chlorobenzoyl)-5-methoxy-2-methylindol-3-ylmethyl]-3-(4-phenylpiperazinomethyl)-1,2,4-oxadiazole, m.p. 133°14 135° C.

5-[1-(4-Chlorobenzoyl)-5-methoxy-2-methylindol-3-ylmethyl]-3-diethylaminomethyl-1,2,4-oxadiazole, m.p. 96°–97° C.

5-[1-(4-Chlorobenzoyl)-5-methoxy-2-methylindol-3-ylmethyl]-3-[di-(n-butyl)aminomethyl]-1,2,4-oxadiazole, m.p. 89°–90° C.

5-[1-(4-Chlorobenzoyl)-5-methoxy-2-methylindol-3-ylmethyl]-3-pyrrolidinomethyl-1,2,4-oxadiazole, m.p. 83.5°–84.5° C.

5-(3-Benzoyl-α-methylbenzyl)-3-pyrrolidinomethyl-1,2,4-oxadiazole, $n_D^{18}$ 1.5767.

EXAMPLE 63

A mixture of 2.14 g of 3-chloromethyl-5-(3-fluoro-4-phenyl-α-methylbenzyl)-1,2,4-oxadiazole, 2.54 g of N,N-diethyl-1-piperazine carboxamide and 15 ml of dry DMF was heated at 100° C. for 2 hours. After cooling, the reaction mixture was poured into ice-water and extracted with diethyl ether. The organic phase was washed with water, dried over magnesium sulfate and evaporated. The residue was chromatographed over silica gel using chloroform-methanol (50:1, v/v) to yield 2.43 g of 3-[4-(N,N-diethylcarbamoyl)piperazinomethyl]-5-(3-fluoro-4-phenyl-α-methylbenzyl)-1,2,4-oxadiazole as a light brown oil. To a solution of this product in ethanol was added equal mole of ethanolic hydrogen chloride and the mixture was concentrated to dryness under reduced pressure. Recrystallization of the residue from ethanol-diethyl ether gave colorless crystals, m.p. 181°–182° C.

EXAMPLE 64

According to substantially the same procedure as that of Example 63, there were obtained the following compounds:

3-(3-Diethylaminopropyl)-5-(3-fluoro-4-phenyl-α-methylbenzyl)-1,2,4-oxadiazole, $n_D^{24}$ 1.5480.

5-(3-Fluoro-4-phenyl-α-methylbenzyl)-3-(imidazol-1-ylmethyl)-1,2,4-oxadiazole, m.p. 83.5°–84° C.

5-[1-(4-Chlorobenzoyl)-5-methoxy-2-methylindol-3-ylmethyl]-3-(imidazol-1-ylmethyl)-1,2,4-oxadiazole oxalate, m.p. 174.5° C. (decomp.).

5-[1-(4-Chlorobenzoyl)-5-methoxy-2-methylindol-3-ylmethyl]-3-(pyrazol-1-ylmethyl)-1,2,4-oxadiazole, m.p. 131.5°–132.5° C.

EXAMPLE 65

A mixture of 6.0 g of 3-chloromethyl-5-(3-fluoro-4-phenyl-α-methylbenzyl)-1,2,4-oxadiazole and 50 ml of liquid ammonia was allowed to stand in an autoclave at room temperature overnight. After evaporation of ammonia, the residue was chromatographed over silica gel using chloroform to give 4.05 g of 3-aminomethyl-5-(3-fluoro-4-phenyl-α-methylbenzyl)-1,2,4-oxadiazole as a light brown oil, $n_D^{22}$ 1.5878.

EXAMPLE 66

To a mixture of 4.13 g of 3-aminomethyl-5-(3-fluoro-4-phenyl-α-methylbenzyl)-1,2,4-oxadiazole, 1.56 g of triethylamine and 60 ml of THF was added dropwise with stirring 3.3 g of α-bromopropionyl bromide at 0°–5° C. After stirring for 1 hour at room temperature, the reaction mixture was diluted with water and extracted with benzene. The organic phase was successively washed with sodium bicarbonate solution and water, dried over sodium sulfate and evaporated. The residue was chromatographed over silica gel using benzene-ethyl acetate (5:1, v/v). Crystallization of the clean fractions from diisopropyl ether yielded 4.88 g of 3-(2-bromopropionylaminomethyl)-5-(3-fluoro-4-phenyl-α-methylbenzyl)-1,2,4-oxadiazole as colorless needles, m.p. 98°–99° C.

EXAMPLE 67

To a solution of 4.58 g of 3-(2-bromopropionylaminomethyl)-5-(3-fluoro-4-phenyl-α-methylbenzyl)-1,2,4-oxadiazole in 60 ml of dry DMF was added 2.42 g of potassium thioacetate. After stirring for 2.5 hours at room temperature, the reaction mixture was poured into ice-water and extracted with benzene. The extracts were washed with water, dried over sodium sulfate and evaporated. The residue was chromatographed over silica gel using benzene-ethyl acetate (6:1, v/v) to yield 4.1 g of 3-(2-acetylthiopropionylaminomethyl)-5-(3-fluoro-4-phenyl-α-methylbenzyl)-1,2,4-oxadiazole as a light brown oil, IR $\nu_{max}^{neat}$ cm$^{-1}$: 3300, 1690, 1670, 1580, 1530, 1485.

EXAMPLE 68

To a solution of 2.95 g of 3-(2-acetylthiopropionylaminomethyl)-5-(3-fluoro-4-phenyl-α-methylbenzyl)-1,2,4-oxadiazole in 50 ml of methanol was added dropwise 18 ml of 40% methylamine solution in methanol at 0°–5° C. After stirring for 20 minutes, the reaction mixture was poured into ice-water, made acidic to pH 3 by addition of 3N hydrochloric acid and extracted with methylene chloride. The extracts were washed with water, dried over sodium sulfate and evaporated. The residue was chromatographed over silica gel using benzene-ethyl acetate (4:1, v/v) to yield 2.1 g of 5-(3-fluoro-4-phenyl-α-methylbenzyl)-3-(2-mercaptopropionylaminomethyl)-1,2,4-oxadiazole as a colorless oil. It was crystallized from diisopropyl ether to give colorless crystals, m.p. 94°–95° C.

EXAMPLE 69

To a solution of 1.0 g of 3-(2-acetylthioethyl)-5-(3-fluoro-4-phenyl-α-methylbenzyl)-1,2,4-oxadiazole in 20 ml of THF was added dropwise with ice-cooling 7 ml of 30% methylamine solution in ethanol. After stirring for 20 minutes, the reaction mixture was concentrated at room temperature under reduced pressure. The solution of the residue in methylene chloride was washed with water, dried over sodium sulfate and evaporated. The resulting crude 3-(2-mercaptoethyl)-5-(3-fluoro-4-phenyl-α-methylbenzyl)-1,2,4-oxadiazole was dissolved in 10 ml of ethanol. The resultant solution was added dropwise with stirring and cooling to a mixture of 0.9 g of 4-picolylchloride, 0.4 g of sodium ethoxide and 10 ml of ethanol. After stirring at room temperature overnight, the reaction mixture was poured into ice-water and extracted with methylene chloride. The organic phase was washed with water, dried over sodium sulfate and evaporated. The residue was chromatographed over silica gel using chloroform to give 0.4 g of 5-(3-fluoro-4-phenyl-α-methylbenzyl)-3-[2-(4-picolylthio)ethyl]-1,2,4-oxadiazole as a colorless oil, IR $\nu_{max}^{neat}$ cm$^{-1}$: 1600, 1590, 1490, 1420.

EXAMPLE 70

A mixture of 0.2 g of 5-(3-fluoro-4-phenyl-α-methylbenzyl)-3-(2-methylthioethyl)-1,2,4-oxadiazole and 2 ml of methyl iodide was stirred and refluxed for 10 hours. After the mixture was concentrated to dryness under reduced pressure, the residue was triturated with diethyl ether, collected by filtration and dried to give [5-(3-fluoro-4-phenyl-α-methylbenzyl)1,2,4-oxadiazol-3-ylethyl]dimethylsulfonium iodide as light yellow fine crystals, m.p. 196.5° C. (decomp.).

EXAMPLE 71

A mixture of 1.5 g of 5-[1-(4-chlorobenzoyl)-5-methoxy-2-methylindol-3-ylmethyl]-3-pyrrolidinomethyl-1,2,4-oxadiazole, 20 ml of chloroform and 5 ml of methyl iodide was stirred for 1 hour at room temperature. The precipitated material was collected, washed with chloroform and dried to give 1-[5-[1-(4-chlorobenzoyl)-5-methoxy-2-methylindol-3-ylmethyl]-1,2,4-oxadiazol-3-ylmethyl]-1-methylpyrrolidinium iodide as colorless fine crystals, m.p. 201.5° C. (decomp.).

What is claimed is:

1. A compound of the formula

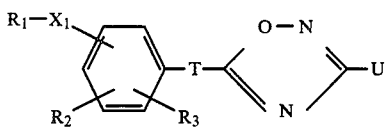

wherein $R_1$ is phenyl or substituted phenyl; $R_2$ and $R_3$ are independently hydrogen or halogen; $X_1$ is the radical $>C=O$ or $-NH-$ or a single bond; T is lower alkylene; and U is hydrogen, lower alkyl, lower alkenyl, polyhalo-lower alkyl, lower cycloalkyl, lower cycloalkenyl, pyridyl, a group of the formula $R_{12}-T_1-$ (wherein $R_{12}$ is halogen, hydroxy, mercapto, lower alkylsulfinyl, di-lower alkoxymethyl, lower alkoxycarbonyl, carboxy, sulfo, cyano, the group

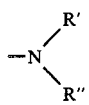

(wherein R' and R'' may be the same of different, and are hydrogen, lower alkyl or hydroxy-lower alkyl, and when taken together with the adjacent nitrogen atom, they may form a 5- or 6-membered saturated or unsaturated heterocyclic ring, which may contain another nitrogen or oxygen atom, or may form a quaternary ammonium salt or N-oxide) or the group

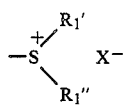

wherein $R_1'$ and $R_1''$ may be the same or different, and are lower alkyl or lower alkenyl; and X is a negative monovalent ion; and $T_1$ is lower alkylene or lower alkenylene, both of which may bear an oxo or a hydroxy group on their carbon chains), or a group of the formula $R_{13}-X_4-T_1-$ (wherein $R_{13}$ is lower alkyl, lower alkenyl, hyroxy-lower alkyl, acyloxy-lower alkyl, amino-lower alkyl, acylamino-lower alkyl, lower cycloalkyl, lower cycloalkenyl, phenyl, substituted phenyl, phenyl-lower alkyl, heterocyclic group, heterocyclic-lower alkyl, acyl, acylthio-lower alkanoyl, mercapto-lower alkanolyl, lower alkoxycarbonyl, lower alkylsulfonyl, the group

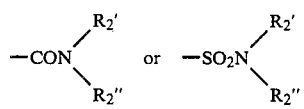

(wherein $R_2'$ and $R_2''$ are independently hydrogen, lower alkyl or hydroxy-lower alkyl); $X_4$ is the radical $-O-$, $-S-$, $-NH-$,

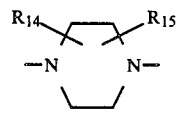

(wherein $R_{14}$ and $R_{15}$ are independently hydrogen or lower alkyl) or a single bond; and $T_1$ is as defined above), wherein:

(a) said substituted phenyl is selected from the group consisting essentially of a phenyl group substituted by halogen, trifluromethyl, $C_{1-6}$ alkyl, $C_{1-6}$ alkoxy and $C_{1-6}$ alkanoylamino;

(b) said heterocyclic group is selected from the group consisting essentially of pyridyl, thienyl, furyl, thiazoyl, imidazoyl, pyrazolyl, pyrrolyl, dihydropyrrolyl, pyrrolidinyl, oxazolyl, oxadiazolyl, benzothiazolyl, dihydrobenzothiazolyl, benzoxazolyl, isoindolinyl, idazopyridyl, piperidyl, morphlinyl, pyrimidyl or pyridazinyl, which may optionally be substituted by haogen, $C^{16}$ alkyl, amino, oxo, and phenyl;

(c) said substituted benzoyl is selected from the group consisting esentially of a benzoyl group substituted by halogen, $C_{1-6}$ alkyl, $C_{1-3}$ alkylene-dioxy and $C_{1-6}$ alkylsulfinyl;

(d) said acyl is selected from the group consisting essentially of $C_{2-4}$ alkanoyl, benzoyl, substituted benzoyl as defined in (c) and nicotinoyl;

(e) said substituted styrylidene is selected from the group consisting essentially of a styrylidene group substituted by halogen and $C_{1-6}$ alkylsulfinyl; and wherein (f) the acyl moieties of acyloxy-lower alkyl, acylamino-lower alkyl and acylthio-lower alkyl in $R_{13}$ as well as acyl therein being as defined in (d); and (g) the heterocyclic moiety of heterocyclic-lower alkyl in $R_{13}$ being as defined in (b).

2. A compound according to claim 1 having the formula,

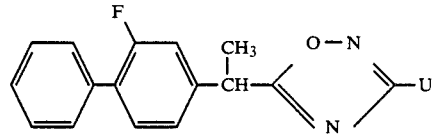

3. A compound according to claim 1 having the formula,

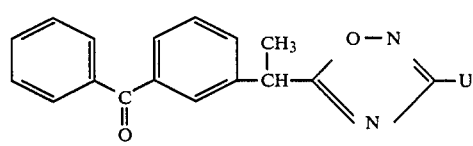

4. A compound according to claim 1 having the formula,

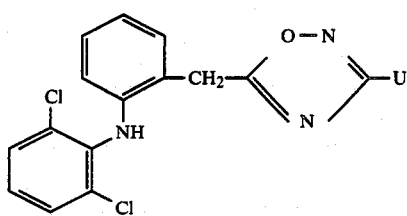

5. A compound having the formula,

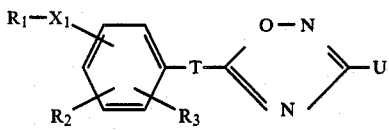

wherein U is hydrogen, lower alkyl, lower alkenyl, polyhalo-lower alkyl, lower cycloalkyl, lower cycloalkenyl, pyridyl, a group of the formula $R_{12}$—$T_1$— (wherein $R_{12}$ is halogen, hydroxy, mercapto, lower alkylsulfinyl, di-lower alkoxymethyl, lower alkoxycarbonyl, carboxy, sulfo, cyano, the group

(wherein R' and R" may be the same or different, and are hydrogen, lower alkyl or hydroxy-lower alkyl, and when taken together with the adjacent nitrogen atom, they may form a 5- or 6-membered saturated or unsaturated heterocyclic ring, which may contain another nitrogen or oxygen atom, or may form a quaternary ammonium salt or N-oxide) or the group

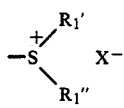

wherein $R_1'$ and $R_1''$ may be the same of different, and are lower alkyl or lower alkenyl; and X is a negative monovalent ion; and $T_1$ is lower alkylene or lower alkenylene, both of which may bear an oxo or a hydroxy group on their carbon chains), or a group of the formula $R_{13}$—$X_4$—$T_1$— (wherein $R_{13}$ is lower alkyl, lower alkenyl, hydroxy-lower alkyl, acyloxy-lower alkyl, amino-lower alkyl, acylamino-lower alkyl, lower cycloalkyl, lower cycloalkenyl, phenyl, substituted phenyl, phenyl-lower alkyl, heterocyclic group, heterocyclic-lower alkyl, acyl, acylthio-lower alkanoyl, mercapto-lower alkanoyl, lower alkoxycarbonyl, lower alkylsulfonyl, the group

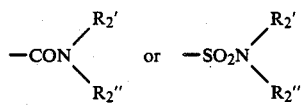

(wherein $R_2'$ and $R_2''$ are independently hydrogen, lower alkyl or hydroxy-lower alkyl); $X_4$ is the radical —O—, —S—, —NH—,

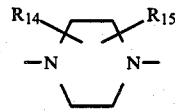

(wherein $R_{14}$ and $R_{15}$ are independently hydrogen or lower alkyl) or a single bond; and $T_1$ is as defined above), wherein:

(a) said substituted phenyl is selected from the group consisting essentially of a phenyl group substituted by halogen, trifluoromethyl, $C_{1-6}$ alkyl, $C_{1-6}$ alkoxy and $C_{1-6}$ alkanoylamino;

(b) said heterocyclic group is selected from the group consisting essentially of pyridyl, thienyl, furyl thiazoyl, imidazoyl, pyrazolyl, pyrrolyl, dihydropyrrolyl, pyrrolidinyl, oxazolyl, oxadiazolyl, benzothiazolyl, dihydrobenzothiazolyl, benzoxazolyl, isoindolinyl, imidazopyridyl, piperidyl, morphinyl, pyrimidyl or pyridazinyl, which may optionally be substituted by halogen, $C_{1-6}$ alkyl, amino, oxo, and phenyl;

(c) said substituted benzoyl is selected from the group consisting essentially of a benzoyl group substituted by halogen, $C_{1-6}$ alkyl, $C_{1-3}$ alkylene-dioxy and $C_{1-6}$ alkylsulfinyl;

(d) said acyl is selected from the group consisting essentially of $C_{2-4}$ alkanoyl, benzoyl, substituted benzoyl as defined in (c) and micotinoyl;

(e) said substituted styrylidene is selected from the group consisting essentially of a styrylidene group substituted by halogen and $C_{1-6}$ alkylsulfinyl; and wherein (f) the acyl moieties of acyloxy-lower alkyl-lower alkyl, acylamino-lower alkyl and acylthio-lower alkyl in $R_{13}$ as well as acyl therein being as defined in (d); and (g) the heterocyclic moiety of heterocyclic-lower alkyl in $R_{13}$ being as defined in (b).

6. A compound having the formula,

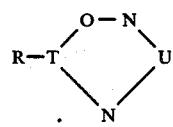

and a pharmaceutically acceptable salt thereof, wherein R is

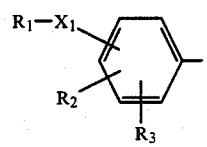

wherein $R_1$ is lower alkyl, lower alkenyl, lower cycloalkyl, lower cycloalkenyl, phenyl, substituted phenyl or heterocyclic group; $R_2$ and $R_3$ are independently hydrogen, halogen, amino, hydroxy, lower alkoxy or lower alkyl; and $X_1$ is the radical —$CH_2$—, —$CH_2O$—, >C=O, —O—, —S— or —NH—, or a single bond;

T is lower alkylene or lower alkenylene, both of which may bear an oxo, ahydroxy or a lower alkoxy radical on their carbon chains; and wherein U is hydrogen, lower alkyl, hydroxy-lower alkyl mercapto-lower alkyl,

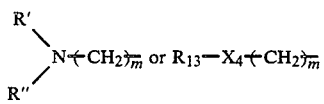

(wherein $R_{13}$ is lower alkyl, hydroxy-lower alkyl, picolyl, acyl or mercapto-lower alkanoyl; $X_4$ is —O—, —S—, —NH— or

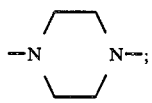

and m is 1, 2 or 3).

7. The compound according to claim 2, which is 5-(3-fluoro-4-phenyl-α-methybenzyl)-3-methyl-1,2,4-oxadiazole.

8. The compound according to claim 2, which is 5-(3-fluoro-4-phenyl-α-methylbenzyl)-isobutyl-1,2,4-oxadiazole.

9. The compound according to claim 2, which is 3-dimethylaminomethyl-5-(3-fluoro-4-phenyl-α-methylbenzyl)-1,2,4-oxadiazole.

10. The compound according to claim 2, which is 5-(3-fluoro-4-phenyl-α-methylbenzyl)-3-pyrrolidinomethyl-1,2,4-oxadiazole.

11. The compound according to claim 3, which is 5-(3-benzoyl-α-methylbenzyl)-3-methyl-1,2,4-oxadizole.

12. The compound according to claim 3, which is 5-(3-benzoyl-α-methylbenzyl)-3-isobutyl-1,2,4oxadiazole.

13. The compound according to claim 3, which is 5-(3-benzoyl-α-methylbenzyl)-3-pyrrolidinomethyl-1,2,4-oxadiazole.

14. The compound according to claim 4, which is 5-[2-(2,6-dichloroanilino)benzyl]-3-isobutyl-1,2,4-oxadiazole.

15. The compound according to claim 5, which is 3-methyl-5-[4-(1-oxo-2-isoindolinyl)-α-methylbenzyl]-1,2,4-oxadiazole.

16. A compound according to claim 1, wherein U is hydrogen, lower alkyl, hydroxy-lower alkyl mercapto-lower alkyl,

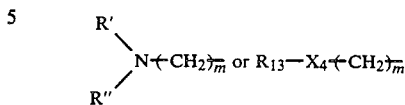

(wherein $R_{13}$ is lower alkyl, hydroxy-lower alkyl, picolyl, acyl or mercapto-lower alkanoyl; $X_4$ is —O—, —S—, —NH— or

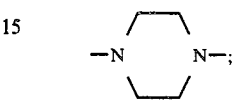

and m is 1, 2 or 3).

17. A compound according to claim 5, wherein U is hydrogen, lower alkyl, hydroxy-lower alkyl mercapto-lower alkyl

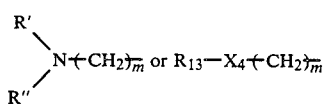

(wherein $R_{13}$ is lower alkyl, hydroxy-lower alkyl, picolyl, acyl or mercapto-lower alkanoyl; $X_4$ is —O—, —S—, —NH— or

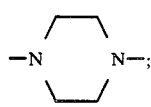

and m is 1, 2 or 3).

18. A pharmaceutical composition which comprises as an active ingredient an anti-inflammatorily or analgesically effective amount of at least one of the compounds of claim 1, 5 or 6 and at least one pharmaceutically acceptable inert carrier or diluent.

* * * * *